(12) United States Patent  
Powell et al.

(10) Patent No.: US 9,108,361 B2
(45) Date of Patent: *Aug. 18, 2015

(54) METHOD FOR MANUFACTURING DENTAL IMPLANT COMPONENTS

(71) Applicant: Biomet 3i, LLC, Palm Beach Gardens, FL (US)

(72) Inventors: Theodore M. Powell, Palm Beach Gardens, FL (US); John T. Amber, Jupiter, FL (US); Bruce Berckmans, III, Palm Beach Gardens, FL (US); Zachary B. Suttin, Jupiter, FL (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/491,510

(22) Filed: Sep. 19, 2014

(65) Prior Publication Data

US 2015/0045925 A1 Feb. 12, 2015

Related U.S. Application Data

(60) Continuation of application No. 13/439,545, filed on Apr. 4, 2012, now Pat. No. 8,855,800, which is a division of application No. 11/921,818, filed as application No. PCT/US2006/025292 on Jun. 29, 2006, now Pat. No. 8,185,224.

(60) Provisional application No. 60/695,501, filed on Jun. 30, 2005.

(51) Int. Cl.
*B29C 67/00* (2006.01)
*A61C 8/00* (2006.01)

(Continued)

(52) U.S. Cl.
CPC ............... *B29C 67/0088* (2013.01); *A61C 8/00* (2013.01); *A61C 8/0001* (2013.01); *A61C 9/008* (2013.01);

(Continued)

(58) Field of Classification Search
USPC ....................................... 700/98; 433/72, 173
See application file for complete search history.

(56) References Cited

U.S. PATENT DOCUMENTS 3,906,634 A 9/1975 Aspel
3,919,772 A 11/1975 Lenczycki (Continued)

FOREIGN PATENT DOCUMENTS

DE 10029256 11/2000 ............... A61C 1/08
WO WO 94/26200 11/1994

(Continued)

OTHER PUBLICATIONS

Biomet 3i—Manual entitled "Navigator™ System For CT Guided Surgery Manual", Revision A Oct. 2007—34 pages.

(Continued)

*Primary Examiner* — Robert Fennema
*Assistant Examiner* — Anthony Whittington
(74) *Attorney, Agent, or Firm* — Nixon Peabody LLP

(57) ABSTRACT

A method for making a rapid prototype of a patient's mouth to be used in the design and fabrication of a dental prosthesis. An intra-oral scan is made of the patient's mouth having an installation site with a dental implant installed and a healing abutment attached to the dental implant. The healing abutment has at least one informational marker. Scan data is generated from the scanning. The scan data is transferred to a CAD program. A three-dimensional model of the installation site is created in the CAD program. The at least one informational marker and the three-dimensional model are used to manufacture a rapid prototype model of the patient's mouth, which includes a dental implant analog.

32 Claims, 20 Drawing Sheets

(51) Int. Cl.
   *A61C 13/00*   (2006.01)
   *A61C 9/00*    (2006.01)
   *A61C 13/34*   (2006.01)
   *G06F 17/50*   (2006.01)

(52) U.S. Cl.
   CPC .......... *A61C 9/0053* (2013.01); *A61C 13/0004* (2013.01); *A61C 13/34* (2013.01); *G06F 17/50* (2013.01); *A61C 13/0013* (2013.01); *A61C 13/0018* (2013.01)

(56) References Cited

U.S. PATENT DOCUMENTS

| | | |
|---|---|---|
| 3,958,471 A | 5/1976 | Muller |
| 4,011,602 A | 3/1977 | Rybicki et al. |
| 4,056,585 A | 11/1977 | Waltke |
| 4,086,701 A | 5/1978 | Kawahara et al. |
| 4,177,562 A | 12/1979 | Miller et al. |
| 4,199,102 A | 4/1980 | Paul |
| 4,294,544 A | 10/1981 | Altschuler et al. |
| 4,306,862 A | 12/1981 | Knox |
| 4,325,373 A | 4/1982 | Slivenko et al. |
| 4,341,312 A | 7/1982 | Scholer |
| 4,364,381 A | 12/1982 | Sher et al. |
| 4,439,152 A | 3/1984 | Small |
| 4,543,953 A | 10/1985 | Slocum et al. |
| 4,547,157 A | 10/1985 | Driskell |
| 4,571,180 A | 2/1986 | Kulick |
| 4,611,288 A | 9/1986 | Duret et al. |
| 4,624,673 A | 11/1986 | Meyer |
| 4,663,720 A | 5/1987 | Duret et al. |
| 4,713,004 A | 12/1987 | Linkow et al. |
| 4,756,689 A | 7/1988 | Lundgren |
| 4,758,161 A | 7/1988 | Niznick |
| 4,767,331 A | 8/1988 | Hoe |
| 4,772,204 A | 9/1988 | Soderberg |
| 4,821,200 A | 4/1989 | Öberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,961,674 A | 10/1990 | Wang et al. |
| 4,964,770 A | 10/1990 | Steinbichler et al. |
| 4,986,753 A | 1/1991 | Sellers |
| 4,988,297 A | 1/1991 | Lazzara et al. |
| 4,988,298 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,087,200 A | 2/1992 | Brajnovic et al. |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary et al. |
| 5,176,516 A | 1/1993 | Koizumi |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic et al. |
| 5,292,252 A | 3/1994 | Nickerson et al. |
| 5,297,963 A | 3/1994 | Dafatry |
| 5,302,125 A | 4/1994 | Kownacki et al. |
| 5,312,254 A | 5/1994 | Rosenlicht |
| 5,312,409 A | 5/1994 | McLaughlin et al. |
| 5,316,476 A | 5/1994 | Krauser |
| 5,320,529 A | 6/1994 | Pompa |
| 5,328,371 A | 7/1994 | Hund et al. |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,350,297 A | 9/1994 | Cohen |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter et al. |
| 5,370,692 A | 12/1994 | Fink |
| 5,372,502 A | 12/1994 | Massen et al. |
| 5,386,292 A | 1/1995 | Massen et al. |
| 5,413,481 A | 5/1995 | Göppel et al. |
| 5,417,569 A | 5/1995 | Perisse |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,516,288 A | 5/1996 | Sichler et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens et al. |
| 5,613,832 A | 3/1997 | Su |
| 5,613,852 A | 3/1997 | Bavitz |
| 5,617,994 A | 4/1997 | Fiedrich |
| 5,630,717 A | 5/1997 | Zuest |
| 5,636,986 A | 6/1997 | Pezeshkian |
| 5,651,675 A | 7/1997 | Singer |
| 5,652,709 A | 7/1997 | Andersson et al. |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |

(56) References Cited

U.S. PATENT DOCUMENTS

| | | |
|---|---|---|
| 5,741,215 A | 4/1998 | D'Urso |
| 5,743,916 A | 4/1998 | Greenberg |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| RE36,126 E | 3/1999 | Beaty et al. |
| 5,876,204 A | 3/1999 | Day et al. |
| 5,885,078 A | 3/1999 | Cagna et al. |
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorio |
| 5,989,258 A | 11/1999 | Hattori |
| 5,992,229 A | 11/1999 | Pyotsia et al. |
| 5,997,681 A | 12/1999 | Kinzie |
| 6,000,939 A | 12/1999 | Ray et al. |
| 6,008,905 A | 12/1999 | Breton et al. |
| 6,050,821 A | 4/2000 | Klaassen et al. |
| RE36,689 E | 5/2000 | Beaty et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,209,794 B1 | 4/2001 | Webster et al. |
| 6,210,162 B1 | 4/2001 | Chishti |
| 6,217,334 B1 | 4/2001 | Hultgren |
| 6,227,859 B1 | 5/2001 | Sutter |
| 6,283,753 B1 * | 9/2001 | Willoughby .............. 433/172 |
| 6,287,119 B1 | 9/2001 | van Nifterick |
| 6,296,483 B1 | 10/2001 | Champleboux |
| 6,305,939 B1 | 10/2001 | Dawood |
| 6,319,000 B1 | 11/2001 | Branemark |
| 6,322,728 B1 | 11/2001 | Brodkin |
| 6,382,975 B1 | 5/2002 | Poirier |
| 6,402,707 B1 | 6/2002 | Ernst |
| 6,431,867 B1 | 8/2002 | Gittelson et al. |
| 6,488,503 B1 | 12/2002 | Lichkus et al. |
| 6,497,574 B1 | 12/2002 | Miller |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,638,219 B1 | 10/2003 | Asch et al. |
| 6,648,640 B2 | 11/2003 | Rubbert et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulman et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |

(56) References Cited

U.S. PATENT DOCUMENTS

| | | | |
|---|---|---|---|
| 7,421,608 B2 | 9/2008 | Schron | |
| 7,425,131 B2 | 9/2008 | Amber et al. | |
| 7,429,175 B2 | 9/2008 | Gittelson | |
| 7,435,088 B2 | 10/2008 | Brajnovic | |
| 7,442,040 B2 * | 10/2008 | Kuo | 433/202.1 |
| 7,476,100 B2 | 1/2009 | Kuo | |
| 7,481,647 B2 | 1/2009 | Sambu et al. | |
| 7,488,174 B2 | 2/2009 | Kopelman et al. | |
| 7,497,619 B2 | 3/2009 | Stoeckl | |
| 7,497,983 B2 | 3/2009 | Khan et al. | |
| 7,520,747 B2 | 4/2009 | Stonisch | |
| 7,522,764 B2 | 4/2009 | Schwotzer | |
| 7,534,266 B2 | 5/2009 | Kluger | |
| 7,536,234 B2 | 5/2009 | Kopelman et al. | |
| 7,545,372 B2 | 6/2009 | Kopelman et al. | |
| 7,551,760 B2 | 6/2009 | Scharlack et al. | |
| 7,555,403 B2 | 6/2009 | Kopelman et al. | |
| 7,556,496 B2 | 7/2009 | Cinader, Jr. et al. | |
| 7,559,692 B2 | 7/2009 | Beckhaus et al. | |
| 7,563,397 B2 | 7/2009 | Schulman et al. | |
| D597,769 S | 8/2009 | Richter et al. | |
| 7,572,058 B2 | 8/2009 | Pruss et al. | |
| 7,572,125 B2 | 8/2009 | Brajnovic | |
| 7,574,025 B2 | 8/2009 | Feldman | |
| 7,578,673 B2 | 8/2009 | Wen et al. | |
| 7,580,502 B2 | 8/2009 | Dalpiaz et al. | |
| 7,581,951 B2 | 9/2009 | Lehmann et al. | |
| 7,582,855 B2 | 9/2009 | Pfeiffer | |
| 7,600,999 B2 * | 10/2009 | Knopp | 433/24 |
| 7,610,910 B2 | 11/2009 | Ahmed | |
| 7,628,537 B2 | 12/2009 | Schulze-Ganzlin | |
| 7,632,097 B2 | 12/2009 | Clerck | |
| 7,653,455 B2 | 1/2010 | Cnader, Jr. et al. | |
| 7,654,823 B2 | 2/2010 | Dadi | |
| 7,655,586 B1 | 2/2010 | Brodkin et al. | |
| 7,658,610 B2 * | 2/2010 | Knopp | 433/24 |
| 7,661,956 B2 | 2/2010 | Powell et al. | |
| 7,665,989 B2 | 2/2010 | Brajnovic et al. | |
| 7,679,723 B2 | 3/2010 | Schwotzer | |
| 7,687,754 B2 | 3/2010 | Eiff et al. | |
| 7,689,308 B2 | 3/2010 | Holzner et al. | |
| D614,210 S | 4/2010 | Basler et al. | |
| 7,698,014 B2 | 4/2010 | Dunne et al. | |
| 7,774,084 B2 | 8/2010 | Cinader, Jr. | |
| 7,780,907 B2 | 8/2010 | Schmidt et al. | |
| 7,785,007 B2 | 8/2010 | Stoeckl | |
| 7,787,132 B2 | 8/2010 | Körner et al. | |
| 7,796,811 B2 | 9/2010 | Orth et al. | |
| 7,798,708 B2 | 9/2010 | Erhardt et al. | |
| 7,801,632 B2 | 9/2010 | Orth et al. | |
| 7,815,371 B2 | 10/2010 | Schulze-Ganzlin | |
| 7,824,181 B2 | 11/2010 | Sers | |
| D629,908 S | 12/2010 | Jerger et al. | |
| 7,855,354 B2 | 12/2010 | Eiff | |
| 7,865,261 B2 | 1/2011 | Pfeiffer | |
| 7,876,877 B2 | 1/2011 | Stockl | |
| 7,901,209 B2 | 3/2011 | Saliger et al. | |
| 7,982,731 B2 | 7/2011 | Orth et al. | |
| 7,985,119 B2 | 7/2011 | Basler et al. | |
| 7,986,415 B2 | 7/2011 | Thiel et al. | |
| 7,988,449 B2 | 8/2011 | Amber et al. | |
| 8,011,925 B2 | 9/2011 | Powell et al. | |
| 8,011,927 B2 | 9/2011 | Merckmans, III et al. | |
| 8,026,943 B2 | 9/2011 | Weber et al. | |
| 8,038,440 B2 | 10/2011 | Swaelens et al. | |
| 8,047,895 B2 | 11/2011 | Basler | |
| 8,057,912 B2 | 11/2011 | Basler et al. | |
| 8,062,034 B2 | 11/2011 | Hanisch et al. | |
| 8,083,522 B2 | 12/2011 | Karkar et al. | |
| 2001/0008751 A1 | 7/2001 | Chishti et al. | |
| 2001/0034010 A1 | 10/2001 | MacDougald et al. | |
| 2002/0010568 A1 | 1/2002 | Rubbert et al. | |
| 2002/0016639 A1 | 2/2002 | Smith et al. | |
| 2002/0028418 A1 | 3/2002 | Farag et al. | |
| 2002/0039717 A1 | 4/2002 | Amber et al. | |
| 2002/0160337 A1 | 10/2002 | Klein et al. | |
| 2002/0167100 A1 | 11/2002 | Moszner | |
| 2003/0130605 A1 | 7/2003 | Besek | |
| 2003/0222366 A1 | 12/2003 | Stangel | |
| 2004/0029074 A1 | 2/2004 | Brajnovic | |
| 2004/0048227 A1 | 3/2004 | Brajnovic | |
| 2004/0180308 A1 | 9/2004 | Ebi et al. | |
| 2004/0193326 A1 | 9/2004 | Phillips et al. | |
| 2004/0219477 A1 | 11/2004 | Harter | |
| 2004/0219479 A1 | 11/2004 | Malin et al. | |
| 2004/0219490 A1 | 11/2004 | Gartner et al. | |
| 2004/0220691 A1 | 11/2004 | Hofmeister et al. | |
| 2004/0229185 A1 * | 11/2004 | Knopp | 433/24 |
| 2004/0241611 A1 | 12/2004 | Amber et al. | |
| 2004/0243481 A1 | 12/2004 | Bradbury et al. | |
| 2004/0253562 A1 * | 12/2004 | Knopp | 433/24 |
| 2004/0259051 A1 | 12/2004 | Brajnovic | |
| 2005/0023710 A1 | 2/2005 | Brodkin et al. | |
| 2005/0042569 A1 * | 2/2005 | Phan et al. | 433/24 |
| 2005/0056350 A1 | 3/2005 | Dolabdjian et al. | |
| 2005/0064360 A1 * | 3/2005 | Wen et al. | 433/24 |
| 2005/0070782 A1 | 3/2005 | Brodkin | |
| 2005/0084144 A1 | 4/2005 | Feldman | |
| 2005/0100861 A1 | 5/2005 | Choi et al. | |
| 2005/0170311 A1 | 8/2005 | Tardieu et al. | |
| 2005/0214714 A1 * | 9/2005 | Wohrle | 433/173 |
| 2005/0271996 A1 | 12/2005 | Sporbert et al. | |
| 2005/0277089 A1 | 12/2005 | Brajnovic | |
| 2005/0277090 A1 | 12/2005 | Anderson et al. | |
| 2005/0277091 A1 | 12/2005 | Andersson et al. | |
| 2005/0282106 A1 | 12/2005 | Sussman et al. | |
| 2005/0283065 A1 | 12/2005 | Babayoff | |
| 2006/0006561 A1 | 1/2006 | Brajnovic | |
| 2006/0008763 A1 | 1/2006 | Brajnovic | |
| 2006/0008770 A1 | 1/2006 | Brajnovic et al. | |
| 2006/0084030 A1 * | 4/2006 | Phan et al. | 433/72 |
| 2006/0093988 A1 | 5/2006 | Swaelens et al. | |
| 2006/0094951 A1 | 5/2006 | Dean et al. | |
| 2006/0127848 A1 | 6/2006 | Sogo et al. | |
| 2006/0154207 A1 * | 7/2006 | Kuo | 433/202.1 |
| 2006/0210949 A1 | 9/2006 | Stoop | |
| 2006/0257817 A1 * | 11/2006 | Shelton | 433/75 |
| 2006/0263741 A1 | 11/2006 | Imgrund et al. | |
| 2006/0278663 A1 | 12/2006 | Mink et al. | |
| 2006/0281041 A1 | 12/2006 | Rubbert et al. | |
| 2007/0009855 A1 * | 1/2007 | Stonisch | 433/215 |
| 2007/0015111 A1 | 1/2007 | Kopelman et al. | |
| 2007/0031790 A1 | 2/2007 | Raby et al. | |
| 2007/0065777 A1 | 3/2007 | Becker | |
| 2007/0077532 A1 | 4/2007 | Harter | |
| 2007/0092854 A1 | 4/2007 | Powell et al. | |
| 2007/0141525 A1 | 6/2007 | Cinader, Jr. | |
| 2007/0211081 A1 | 9/2007 | Quadling et al. | |
| 2007/0218426 A1 | 9/2007 | Quadling et al. | |
| 2007/0269769 A1 | 11/2007 | Marchesi | |
| 2007/0281277 A1 | 12/2007 | Brajnovic | |
| 2008/0015740 A1 | 1/2008 | Osann | |
| 2008/0038692 A1 | 2/2008 | Andersson et al. | |
| 2008/0044794 A1 | 2/2008 | Brajnovic | |
| 2008/0057467 A1 | 3/2008 | Gittelson | |
| 2008/0064005 A1 * | 3/2008 | Meitner | 433/74 |
| 2008/0070181 A1 | 3/2008 | Abolfathi et al. | |
| 2008/0085489 A1 | 4/2008 | Schmitt | |
| 2008/0090210 A1 | 4/2008 | Brajnovic | |
| 2008/0096152 A1 * | 4/2008 | Cheang | 433/24 |
| 2008/0114371 A1 | 5/2008 | Kluger | |
| 2008/0118895 A1 | 5/2008 | Brajnovic | |
| 2008/0124676 A1 | 5/2008 | Marotta | |
| 2008/0153061 A1 | 6/2008 | Marcello | |
| 2008/0153065 A1 | 6/2008 | Brajnovic et al. | |
| 2008/0153069 A1 | 6/2008 | Holzner et al. | |
| 2008/0160485 A1 * | 7/2008 | Touchstone | 433/215 |
| 2008/0161976 A1 | 7/2008 | Stanimirovic | |
| 2008/0166681 A1 * | 7/2008 | Weinstein et al. | 433/76 |
| 2008/0176189 A1 * | 7/2008 | Stonisch | 433/215 |
| 2008/0206714 A1 | 8/2008 | Schmitt | |
| 2008/0233537 A1 | 9/2008 | Amber et al. | |
| 2008/0241798 A1 | 10/2008 | Holzner et al. | |
| 2008/0261165 A1 | 10/2008 | Steingart et al. | |

(56) References Cited

U.S. PATENT DOCUMENTS

| | | |
|---|---|---|
| 2008/0281472 A1 | 11/2008 | Podgorny et al. |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0130630 A1 | 5/2009 | Suttin et al. |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0259343 A1 | 10/2009 | Rasmussen et al. |
| 2009/0263764 A1 | 10/2009 | Berckmans, III et al. |
| 2009/0281667 A1 | 11/2009 | Masui et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0159412 A1* | 6/2010 | Moss et al. ............... 433/24 |
| 2010/0159413 A1* | 6/2010 | Kuo ............................ 433/24 |
| 2010/0173260 A1 | 7/2010 | Sogo et al. |
| 2010/0280798 A1 | 11/2010 | Pattijn et al. |
| 2011/0008751 A1 | 1/2011 | Pettersson |
| 2011/0010014 A1 | 1/2011 | Oexman et al. |
| 2011/0060558 A1 | 3/2011 | Pettersson |
| 2011/0129792 A1 | 6/2011 | Berckmans, III et al. |
| 2011/0183289 A1 | 7/2011 | Powell et al. |
| 2011/0191081 A1 | 8/2011 | Malfliet et al. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2012/0010740 A1 | 1/2012 | Swaelens et al. |

FOREIGN PATENT DOCUMENTS

| | | |
|---|---|---|
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |

OTHER PUBLICATIONS

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).

International Search Report for International Application No. PCT/US06/40951, filed Oct. 19, 2006, dated Sep. 25, 2007(2 pages).

International Search Report for International Application No. PCT/US2009/034463, filed Feb. 19, 2009, dated Apr. 30, 2009 (2 pages).

Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).

Machine Design: "Robots are ready for medical manufacturing." Retrieved from MachineDesign.Com, <URL: http://machinedesign.com/articie/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

Written Opinion of International Application No. PCT/US2009/034463, filed Feb. 19, 2009, dated Apr. 30, 2009 (6 pages).

* cited by examiner

METHOD FOR MANUFACTURING DENTAL IMPLANT COMPONENTS

CROSS REFERENCE TO RELATED APPLICATIONS

This application is a continuation of U.S. patent application Ser. No. 13/439,545, filed Apr. 4, 2012, now allowed, which is a divisional of U.S. patent application Ser. No. 11/921,818, filed Dec. 7, 2007, now issued as U.S. Pat. No. 8,185,224, which is a U.S. national phase of International Application No. PCT/US2006/025292, filed Jun. 29, 2006, which claims the benefit of priority of U.S. Provisional Patent Application No. 60/695,501, filed Jun. 30, 2005, each of which are incorporated by reference in their entireties.

FIELD OF INVENTION

The present invention relates generally to dental implant systems. More particularly, the present invention relates to dental implant systems wherein an implant is implanted in an edentulous bone of the alveolar arches of the jaws.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is made. The impression coping may be a "pick-up" type impression coping or a "transfer" type impression coping, both known in the art. After these processes, a dental laboratory creates a prosthesis to be permanently secured to the dental implant from the impression that was made.

In addition to the method that uses the impression material and mold to manually develop a prosthesis, systems exist that utilize scanning technology to assist in generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and surrounding area is scanned. Third, a dentist or technician can scan the stone model of the dental region that was formed from the impression material and mold to produce the permanent components.

Three basic scanning techniques exist, laser scanning, photographic imaging and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer aided design ("CAD") package.

The utilization of a CAD program, as disclosed in U.S. Pat. No. 5,338,198, (Wu), whose disclosure is incorporated by reference herein, is one method of scanning a dental region to create a three dimensional model. Preferably, after the impression is made of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known location in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known means.

Photographic imaging can also used to scan impression material, a stone model or to scan directly in the mouth. For example, one system takes photographs at multiple angles in one exposure to scan a dental region, create a model and manufacture a prosthetic tooth. As disclosed in U.S. Pat. No. 5,851,115, (Carlsson), whose disclosure is incorporated by reference herein, this process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position and other details of the model, the ultimate step is the transmission of the data to a computer for manufacturing.

A third scanning measure uses mechanical sensing. A mechanical contour sensing device, as disclosed in U.S. Pat. No. 5,652,709 (Andersson), whose disclosure is incorporated by reference herein, is another method used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer then compresses the data for storage and/or transmission to the milling equipment.

When the stone model of the patient's mouth is created for use in the scanning process, or in other prior techniques, a second stone model of the patient's mouth is also required to develop a final prosthesis for use in the patient. Unfortunately, accuracy limitations on the second stone model reduce the precision of the final prosthesis. A need exists for a method that eliminates the need to create this second stone model.

SUMMARY OF THE INVENTION

According to one process of the current invention, a rapid prototype of a patient's dentition and dental implant analog for use in creating a patient specific prosthetic is provided. The process takes an impression of a mouth including a first installation site that has a dental implant installed in the first installation site and a gingival healing abutment that has at least one informational marker attached to the dental implant. A stone model based on the impression is prepared. The stone model includes teeth models and model markers indicative of the at least one informational marker. The process scans scanning the model. Scan data are generated from the scan of the model. The scan data are transferred to a CAD program. The method creates a three-dimensional model of the installation site on the CAD program using the scan data. The process determines the at least one informational marker to gather information for manufacturing the rapid prototype of the patient's dentition. The process develops the rapid prototype dimensional information based on the three-dimensional image and the at least one informational marker. The method transfers the rapid prototype dimensional information to a rapid prototyping machine. The process fabricates the rapid prototype of the patient's dentition and dental implant analog receptacles on the rapid prototyping machine using the rapid prototype dimensional information.

According to another process of the current invention, a method of manufacturing a rapid prototype of a patient's dentition and dental implant analog for use in creating a patient specific prosthesis is provided. The process takes an impression of a mouth including a first installation site that has a dental implant installed in the first installation site and a gingival healing abutment having at least one informational marker attached to the dental implant. The process prepares a stone model based on the impression, the stone model includes teeth models and model markers indicative of the at least one informational marker. The method scans the model. The process generates scan data from the scan of the model. The scan data transfers to a CAD program. The process creates a three-dimensional model of the installation site on the CAD program using the scan data. The method determines the at least one informational marker to gather information for manufacturing the rapid prototype of the patient's dentition. The method develops the rapid prototype dimensional information based on the three-dimensional image and the at least one informational marker. The process obtains soft tissue element dimensional information based on the three-dimensional image and the at least one informational marker. The method generates soft tissue element mold dimensional information based on the soft tissue element dimensional information. The method provides the soft tissue element mold dimensional information to a rapid prototyping machine. The method produces a mold of the soft tissue element on the rapid prototyping machine. The process casts the soft tissue element in the mold of the soft tissue element. The method transfers the rapid prototype dimensional information to a rapid prototyping machine. The method fabricates the rapid prototype of the patient's dentition and dental implant analog receptacles on the rapid prototyping machine using the rapid prototype dimensional information. The method assembles the soft tissue element to the rapid prototype of the patient's dentition and dental implant analog.

According to a further process of the present invention, a method of manufacturing a custom dental prosthesis is provided. The process installs a dental implant into a first installation site in bone having overlying gingiva in a mouth. The method attaches an attachment member to the dental implant. The attachment member has at least one informational marker for identifying physical characteristics of the attachment member. The process takes an impression of the mouth including the first installation site. The method prepares a stone model based on the impression. The stone model includes teeth models and model markers indicative of the at least one informational marker. The method takes an impression of the mouth including the first installation site. The process prepares a stone model based on the impression. The stone model includes teeth models and model markers indicative of the at least one informational marker. The process scans the model. The method generates scan data from the scanning of the model. The process transfers the scan data to a graphical imaging software program. The method creates a three-dimensional image of the installation site. The method determines the model markers to gather information for manufacturing the custom-abutment. The process develops custom-abutment dimensional information based on the three-dimensional image and the information gathered from the at least one informational marker. The method transfers the custom-abutment dimensional information to a milling machine. The process fabricates the custom-abutment on the milling machine utilizing the custom-abutment dimensional information. The method determines the at least one informational marker to gather information for manufacturing a rapid prototype of the patient's mouth, including information regarding the dental implant. The process develops the rapid prototype dimensional information based on the three-dimensional image and the at least one informational marker. The method transfers the rapid prototype dimensional information to a rapid prototyping machine. The method fabricates the rapid prototype of the patient's mouth and dental implant analog receptacle on the rapid prototyping machine using the rapid prototype dimensional information. The process attaches the custom abutment to the dental implant analog on the rapid prototype of the patient's mouth and dental implant analog. The method produces a tooth-like prosthetic adapted to mate with the custom abutment.

According to yet another process of the present invention, method to create a dental laboratory model upon which a final prosthetic tooth can be created is provided. The method scans a model of a patient's mouth that has a replicated portion of a healing abutment. The method creates a CAD model from data acquired by the scan. The method uses a rapid prototype technique to create the dental laboratory model from the CAD model. The dental laboratory model includes an implant analog at a location corresponding to the replicated portion of the healing abutment.

According to yet a further process of the present invention, a method to create a dental laboratory model upon which a final prosthetic tooth can be created is provided. The method scans a patient's mouth including a portion of a healing abutment. The method creates a CAD model from data acquired by the scan. The method uses a rapid prototype technique to create the dental laboratory model from the CAD model. The dental laboratory model includes an implant analog at a location corresponding to the portion of the healing abutment.

According to still yet another process of the present invention, a method to create a final prosthesis for an implantation sit in a patient's mouth is provided. The method takes an impression of the patient's mouth at the implantation site. The impression includes an impressed area corresponding to a healing abutment attached to an implant at the implantation site. The process creates a stone model from the impression. The method develops a computer model from the stone model. The method creates a custom dental abutment on the computer model. The method creates a rapid prototype model from the computer model. The method attaches the dental abutment to the rapid prototype model. The process forms tooth-like material around the abutment.

According to one embodiment of the present invention, a dental component comprises a rapid prototype model created from a CAD image of a physical model of a patient's mouth and includes an implant analog at a location substantially corresponding to a region in the patient's mouth adjacent to the dental implant.

According to another embodiment of the present invention, a dental component comprises a rapid prototype model created from a CAD image of a physical model of a patient's mouth and includes a soft tissue element at a region substantially corresponding to a region in the patient's mouth adjacent to a dental implant and further includes an implant analog at a location substantially corresponding to a region in the patient's mouth adjacent to the dental implant.

According to a further embodiment of the present invention, a dental component comprises a rapid prototype model created from a CAD image of a patient's mouth and includes an implant analog at a location substantially corresponding to a region in the patient's mouth adjacent to a dental implant.

According to yet another embodiment of the present invention, a dental component comprises a rapid prototype model created from a CAD image of a patient's mouth and includes a soft tissue element at a region substantially corresponding to a region in the patient's mouth adjacent to a dental implant and further includes an implant analog at a location substantially corresponding to a region in the patient's mouth adjacent to the dental implant.

BRIEF DESCRIPTION OF THE DRAWINGS

FIG. 1b is a longitudinal cross-sectional view of the healing abutment shown in FIG. 1a;
FIG. 2b is a longitudinal cross-sectional view of the healing abutment shown in FIG. 2a;
FIG. 3b is a longitudinal cross-sectional view of the healing abutment shown in FIG. 3a;
FIG. 4b is a longitudinal cross-sectional view of the healing abutment shown in FIG. 4a;

FIG. 5b is a longitudinal cross-sectional view of the healing abutment shown in FIG. 5a;
FIG. 6b is a longitudinal cross-sectional view of the healing abutment shown in FIG. 6a.

Figure 1A:
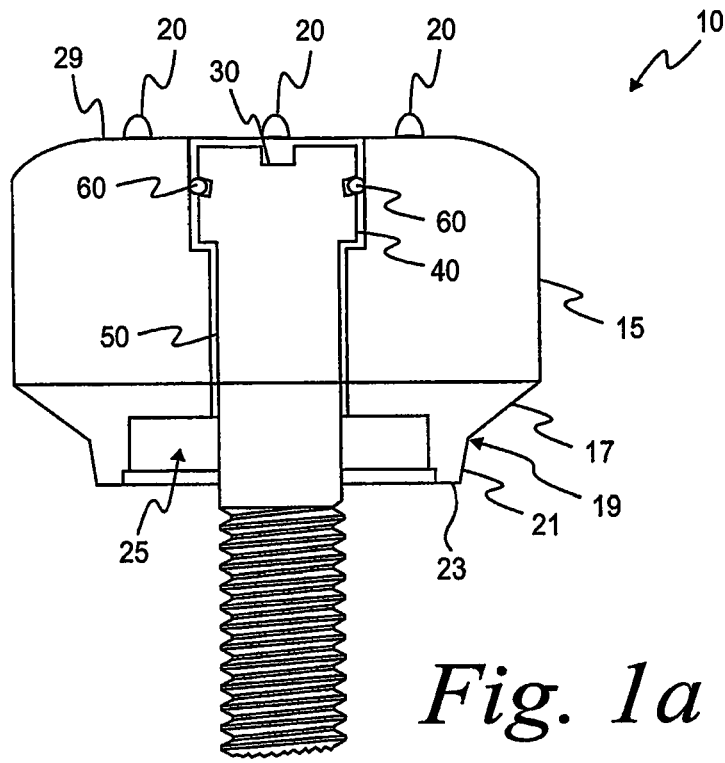
FIG. 1a is a top view of a healing abutment.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1B:
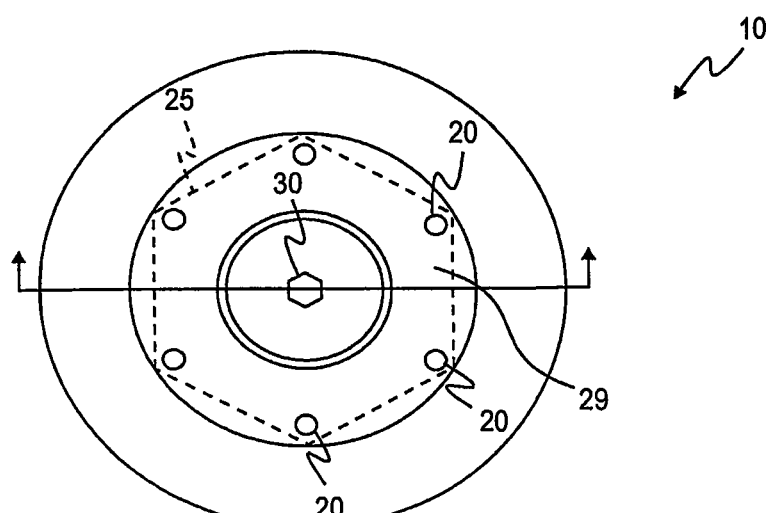

As shown in FIGS. 1a and 1b, the healing abutment 10 of one embodiment of the present invention has a main body 15 with a generally circular cross-sectional shape, a first tapered section 17, a boundary 19, a second tapered section 21, an end surface 23, a hex socket 25 and dimensions that are generally suitable for replicating the emergence profile of a natural tooth. The first tapered section 17 extends downwardly from the main body 15 of the abutment 10 having a diameter at a boundary 19 that is generally larger than the implant (not shown). The boundary 19 separates the first tapered section 17 from the second tapered section 21 that terminates in the end surface 23. The second tapered section 21 is at an angle with the central axis of the implant that is generally in the range from about 5 degrees to about 15 degrees, with 10 degrees being preferable. Alternatively, the second tapered section 21 may be omitted such that the first tapered section 17 tapers directly to the diameter of the end surface 23 of the implant. In a further embodiment, the first tapered section 17 may merge smoothly into the second tapered section 21, without the distinct boundary 19 separating the two tapered sections 17 and 21. The hexagonal orientation socket or hex 25 is for mating with a hexagonal boss on the implant. The end surface 23 has generally the same diameter as the seating surface of the implant.

FIG. 1b discloses the top view of the same healing abutment 10 shown in FIG. 1a. As shown in FIGS. 1a and 1b, the healing abutment 10 has positive information markers 20 protruding from a top surface 29 of the healing abutment 10. Each of the six positive information markers 20 is disposed such that it aligns with the six corners of the underlying hex 25. It is also contemplated in accordance with the present invention that the six information markers 20 may also correspond to the height of the healing abutment. For example, two information markers might correspond to a 2 mm tall healing abutment and four information markers might correspond to a healing abutment that is 4 mm tall. In these embodiments, the two or four information markers would still be at the corners of the underlying hex 25 so that the relative position of the hex is known.

Figure 1C:
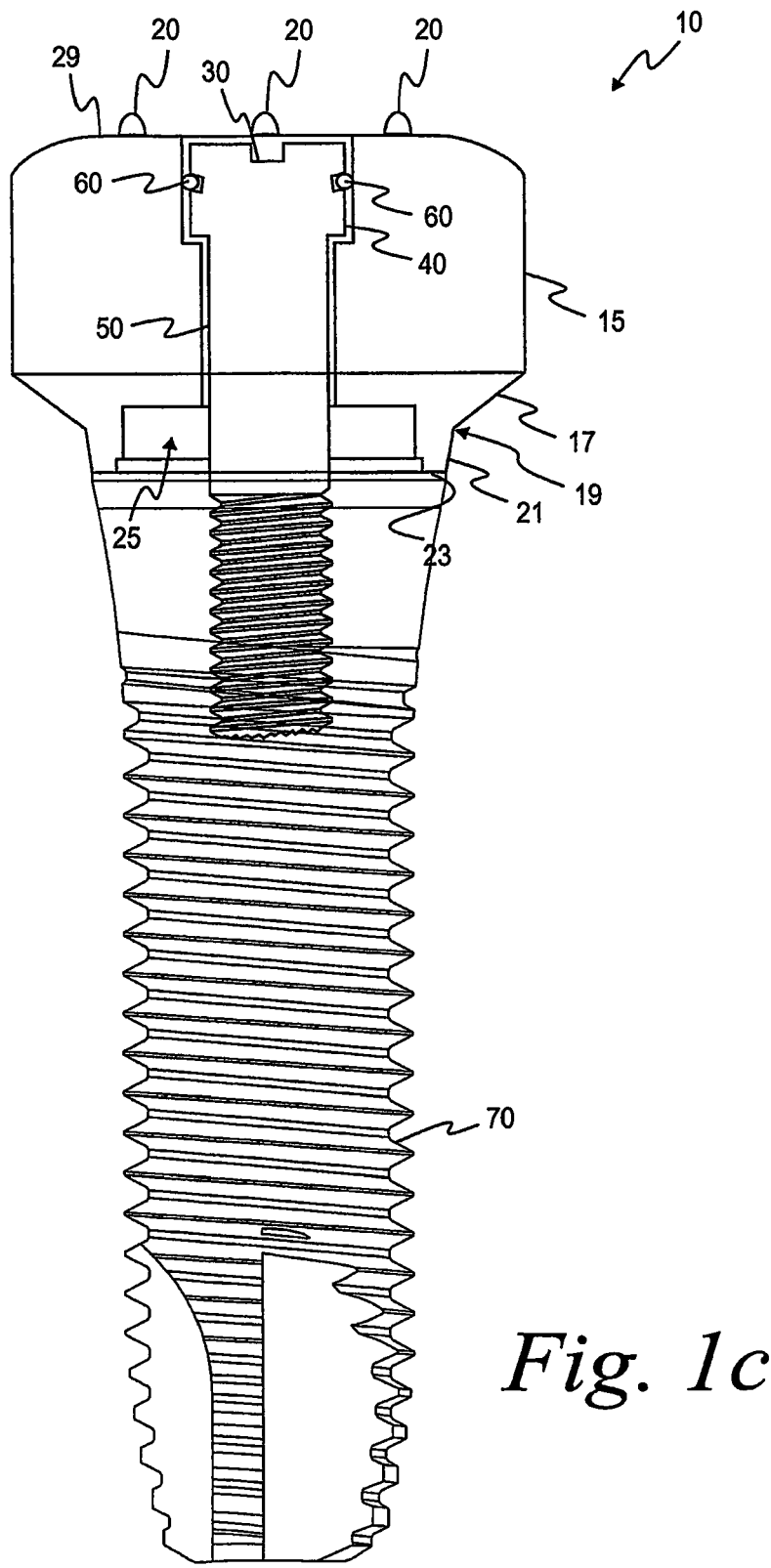
FIG. 1c is the healing abutment shown in FIG. 1b attached to an implant.

A socket 30 on the exposed surface of a head portion 40 of an attaching bolt 50 is shaped to accept a wrench (not shown) for turning the attaching bolt 50 into the threaded bore of an implant 70, as shown in FIG. 1c. It is contemplated in accordance with the present invention that each of the healing abutments described herein and shown in the figures can be secured to an implant by means of an attaching bolt, as is known in the art. An O-ring 60 carried on the head portion 40 of the attaching bolt 50 fills an annular gap left between the head and the entrance section near the outermost (widest) opening in the entrance section.

Figure 2A:
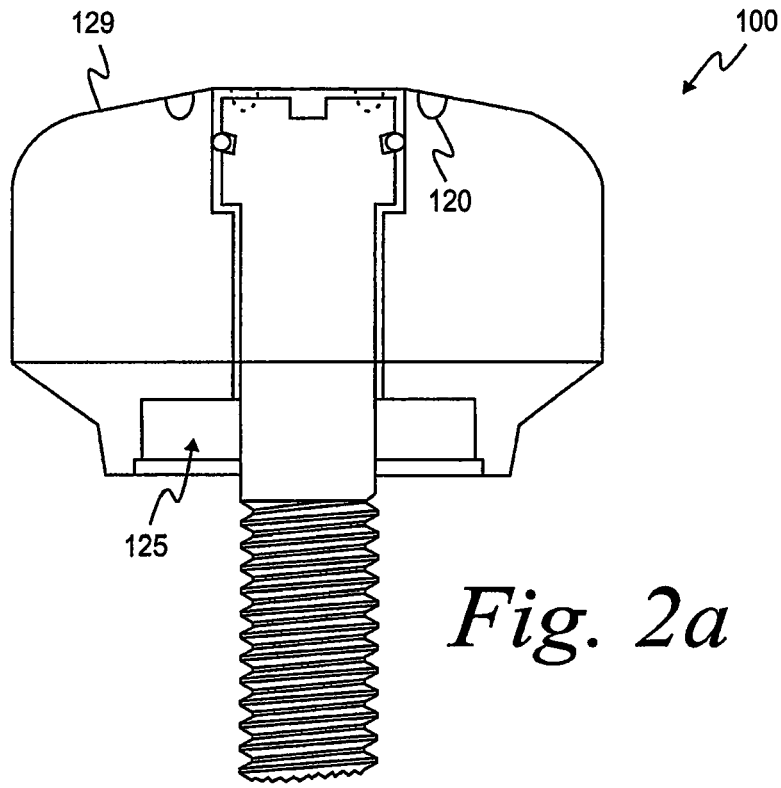
FIG. 2a is a top view of another embodiment of a healing abutment.
Figure 2B:
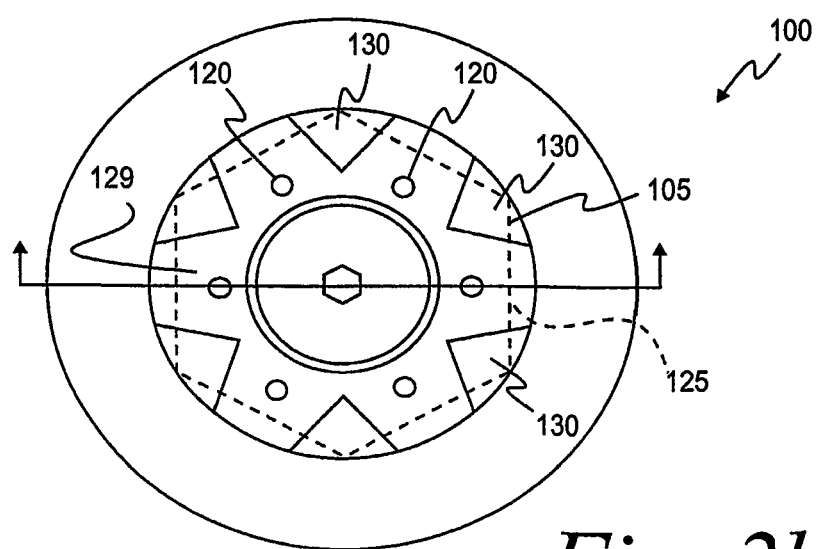

A healing abutment 100 of FIG. 2a comprises many of the same features as the healing abutment 10 shown in FIG. 1a. Dashed lines 125 in FIG. 2b correspond to the underlying hex 125 of the healing abutment 100 in FIG. 2a. A top surface 129 includes negative information markers (recesses) 120 that are displayed in FIG. 2a as dimples extending below the top surface 129 of the healing abutment 100. The top surface 129 of the healing abutment 100 also possesses six notches 130 that are machined into the corners. The top surface 129 is generally flat and merges into a rounded shape at the periphery of the healing abutment 100.

The notches 130 are used, for example, to determine the identification of the underlying implant hex position 125 or the height of the healing abutment or the diameter of the healing abutment. This embodiment is not limited to comprising six notches in the top surface 129 of the healing abutment 100. It is also contemplated that one embodiment of the present invention may possess four notches or even two notches for indicative purposes. Furthermore, it is contemplated that the information marker and notch approach could be combined or modified to provide information regarding the underlying implant seating surface diameter and implant hex angulation.

Figure 3A:
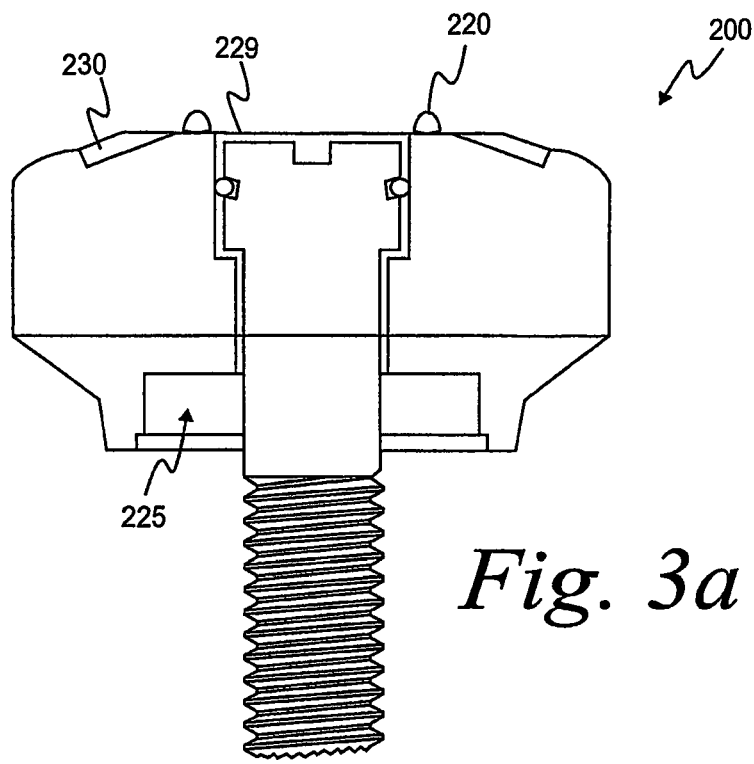
FIG. 3a is a top view of yet another embodiment of a healing abutment.
Figure 3B:
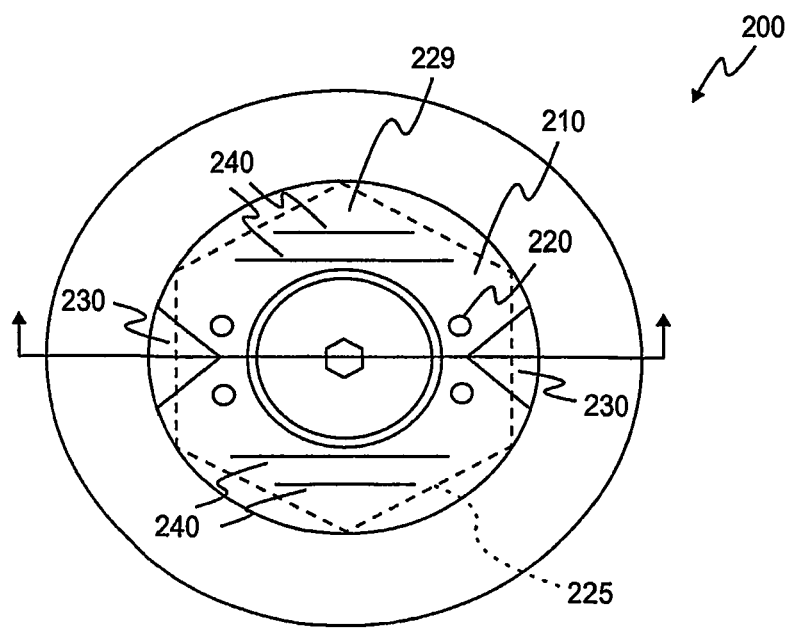

In another embodiment of the present invention, a healing abutment 200 shown in FIGS. 3a and 3b displays four positive information markers 220 shown to, for example, indicate a 4 mm tall healing abutment 200. It is contemplated that the number of information markers 220 could decrease or increase depending on the height of the healing abutment 200 or another variable that the information markers have been designated to correspond. The positive information markers 220 also define a corresponding one of the six flat surfaces of an underlying hex 225. Furthermore, dashed lines 225 in FIG. 3b correspond directly to the underlying hex 225.

Two notches 230 have also been etched or machined onto a top surface 229 of the healing abutment of FIG. 3b. These notches may indicate the diameter of the implant's seating surface. Lines 240 are scribed on the top surface 229 of the healing abutment 200. The lines 240 are used to provide positioning or other information to the dentist or laboratory. Here, the lines 240 indicate the diameter of the healing abutment (e.g., 4 mm). In summary, the number of the positive information markers 220 indicates the height of the healing abutment 200. The position of the positive information markers 220 indicates the orientation of the hex 225 that is the orientation of the hexagonal boss on the implant. The notches 230 indicate the diameter of the seating surface of the implant. The lines 240 indicate the diameter of the healing abutment 200.

Figure 4A:
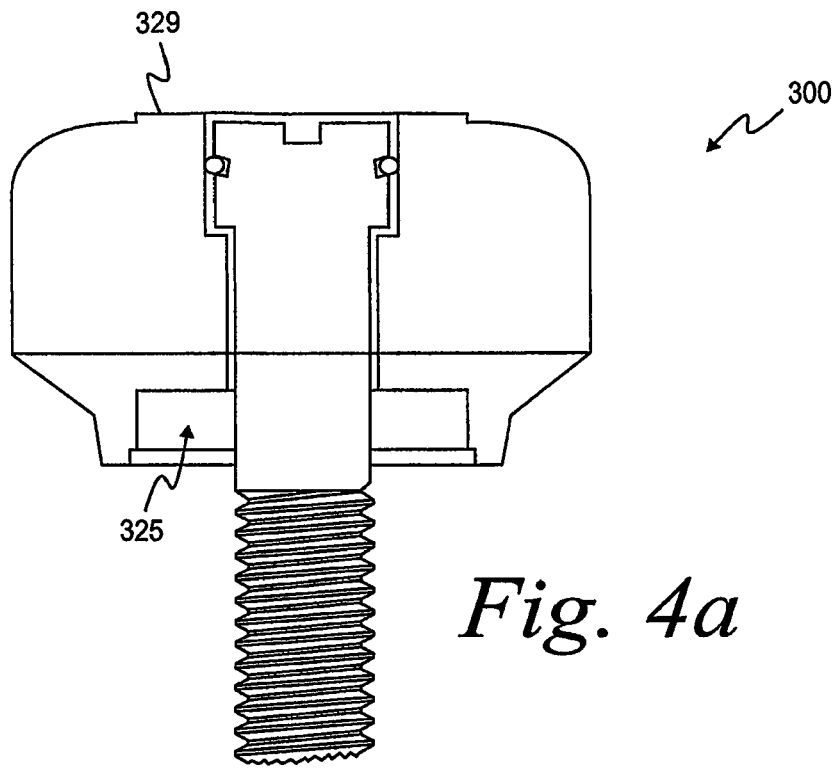
FIG. 4a is a top view of a further embodiment of the healing abutment.
Figure 4B:
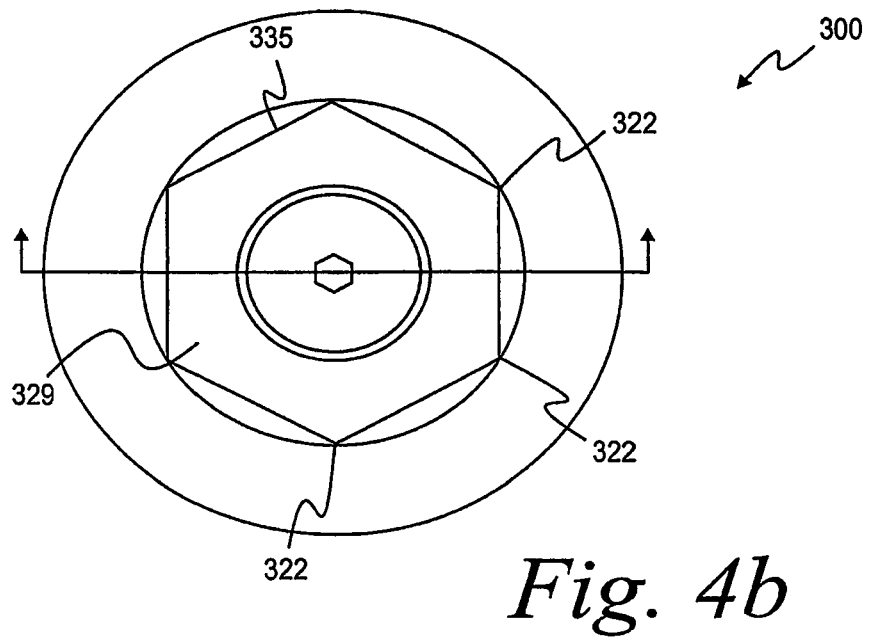

In yet another embodiment of the present invention, a top surface 329 of the healing abutment 300 of FIGS. 4a and 4b comprises an etched or machined hex 335. Corners 322 of the etched hex 335 correspond directly to the position of the corners of an underlying hex 325 shown in FIG. 4a. It is contemplated in accordance with one embodiment of the present invention that further information markers may be added to the healing abutment for the dentist or laboratory to ascertain different heights or diameters.

Figure 5A:
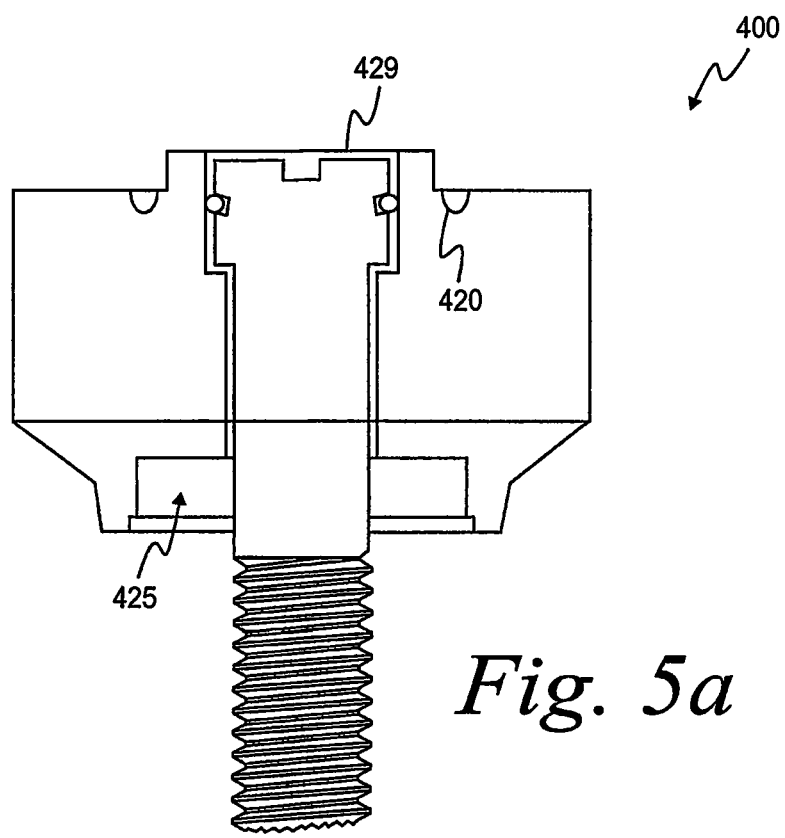
FIG. 5a is a top view of another embodiment of a healing abutment.
Figure 5B:
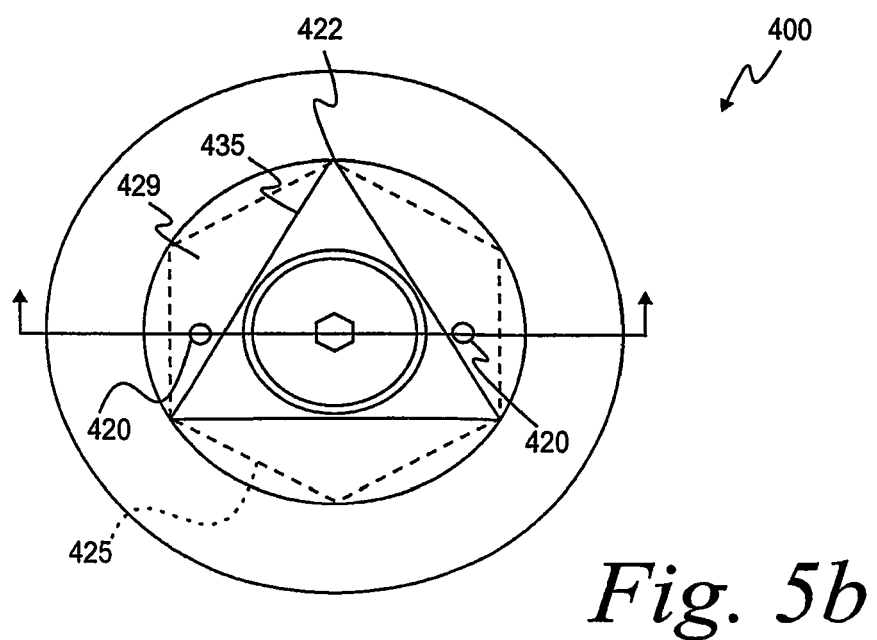

A top surface 429 of a healing abutment 400 shown in FIGS. 5a and 5b contains an etched or machined triangle 435. Dashed lines 425 in FIG. 5b indicate the location of an underlying hex 425. Corners 422 of the etched triangle 435 correspond to three of the six corners of the underlying hex 425. Furthermore, two negative information markers 420 are shown in FIG. 5b. As above, it is contemplated in accordance with the present invention that fewer than six information markers may exist to account for differing heights or diameters of the healing abutments.

Figure 6A:
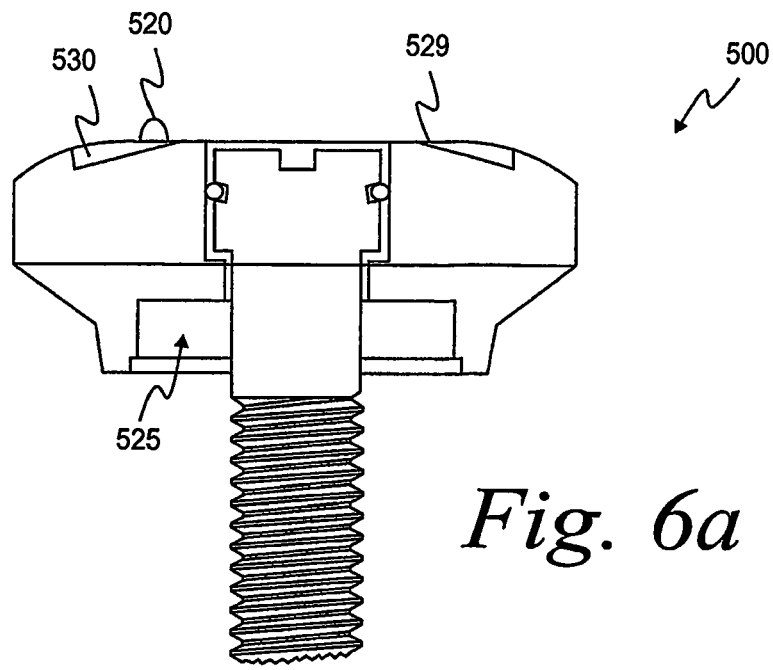
FIG. 6a is a top view of another embodiment of a healing abutment.
Figure 6B:
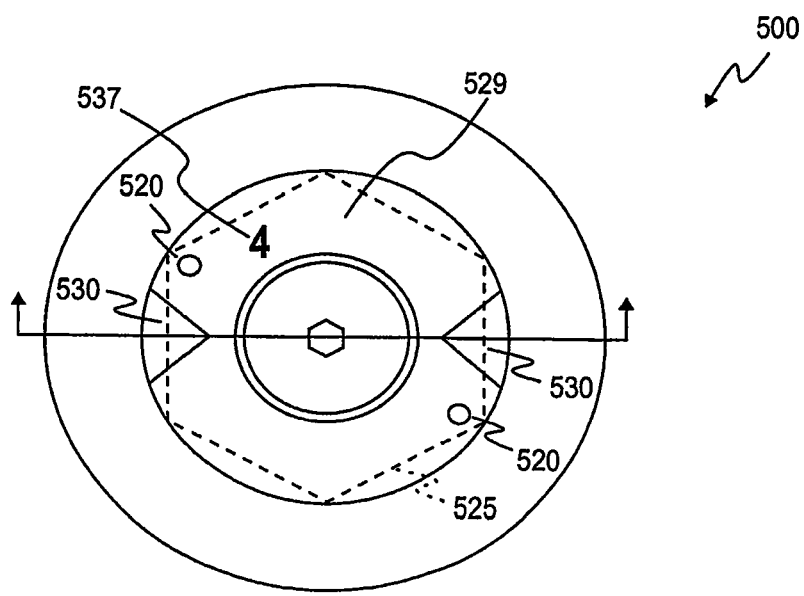

Another embodiment of the present invention is shown in FIGS. 6a and 6b. The healing abutment 500 displayed in FIGS. 6a and 6b is a shorter version of the healing abutment 10 shown in FIGS. 1a and 1b. Two positive information markers 520 are shown in FIG. 6b to identify the height of the healing abutment 500. Dashed lines 525 of the healing abutment 500 correspond with the location and orientation of the underlying hex 525. Two notches 530 are also shown in a top surface 529 of this embodiment of the present invention to show the orientation of two of the underlying flats of the underlying hex 525. A numeral "4" at 537 is located on the top surface 529 of the healing abutment 500 to indicate, for example, the diameter of the healing abutment 500. As shown, the numeral "4" at 537 corresponds to a healing abutment 500 with a diameter of 4 mm. It is contemplated in accordance with the present invention that other numerals could be placed on the top surface 529 of the healing abutment 500 to indicate other healing abutment diameters. Further, it is also contemplated that the numeral could represent the height of the healing abutment or the diameter of the underlying implant.

During the second stage of the prosthetic implementation process and after a healing abutment with the information markers has been placed, an impression of the mouth is made with only the healing abutments as described herein and without the use of an impression coping. A model of the impression is poured with, for example, die stone. Since the information markers are disposed on the top and/or side of the healing abutment, the laboratory has all necessary information to define the gingival aperture, the implant size and the orientation of the underlying hex. This enables the laboratory to quickly prepare the permanent components. The system of the present invention also allows the maintenance of the soft-tissue surrounding the healing abutment where in prior systems the soft tissue would close once the healing abutment was removed. The system spares the patient from the pain of removing the healing abutment.

Figure 8:
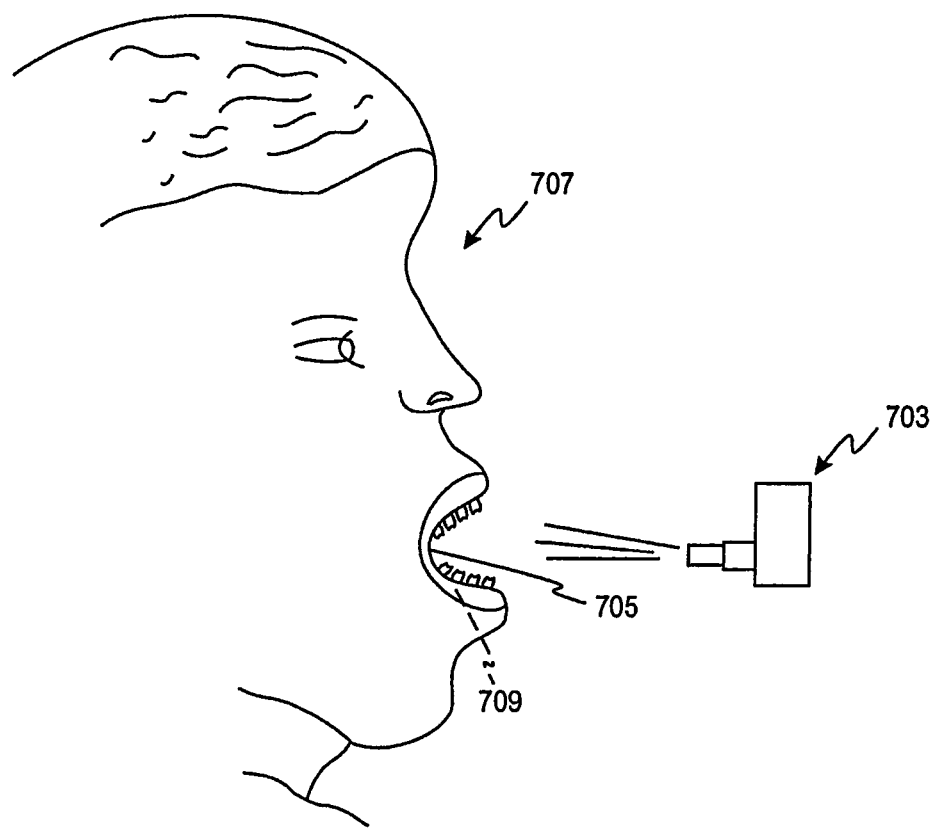
FIG. 8 is a side view of a method for stereophotographic imaging.

To create a permanent prosthesis, the dental region is scanned, as described above, from a stone model, from the impression material, or directly in the mouth using a laser scanning technique, a photographic scanning technique or a mechanical sensing technique. FIG. 8 shows stereophotographic imaging, one method used for scanning. Stereophotography with a camera 703 is performed directly on the mouth cavity 705 of the patient 707. A clinician can photograph implants and other components that have been placed into or adjacent the patient's jawbone 709.

The scanned information is then transferred into a graphical imaging program for analysis. The graphical imaging software program, due to the information markers on the surface of the healing abutment, can perform a wide variety of functions. The graphical imaging program can scan an opposing cast in order to develop an opposing occlusal scheme and relate this information back to the primary model. This feature is extremely important because many clinical patients have implants in both maxillary and mandibular locations.

The graphical imaging software program is capable of generating a three-dimensional image of the emergence profile contours used on the healing abutment. If the implant is not placed in the desired esthetic location, the software program relocates the position of the restoration emergence through the soft tissue. The graphical imaging software program is also able to accurately relate the gingival margin for all mold, model, implant and abutment dimensions. The software creates a transparent tooth outline for superimposition within the edentulous site. The occlusal outline of the "ghost" tooth should, if possible, be accurate and based on the scanned opposing occlusal dimensions. It is contemplated in accordance with the present invention that an occlusal outline is created by scanning a wax-up in order to maintain a proper plane of occlusion and healing abutment height.

The software program subtracts a given dimension from the mesial, distal, buccal, lingual, and occlusal areas of the superimposed tooth dimension. This allows for an even reduction of the healing abutment during fabrication to allow for proper thickness of the overlying materials (e.g., gold, porcelain, targis, etc.). The graphical imaging software program also incorporates angulation measurements into the custom abutment and subsequently calculates the dimensions of the prosthesis that are checked and modified, if necessary, by a laboratory technician. Each of the features is analyzed and determined from the different information markers that exist on the healing abutments of the present invention.

The final dimensional information determined by the graphical imaging computer program is transferred from the computer to a milling machine (e.g., a 5-axis milling machine) to fabricate the custom abutment. It is contemplated in accordance with the present invention that the custom abutment can be fashioned from gold or titanium or other similar metals or composites. A custom milled coping can then be fabricated. It is contemplated in accordance with the present invention that the custom milled coping can be formed from titanium, plastic, gold, ceramic, or other similar metals and composites.

Figure 7:
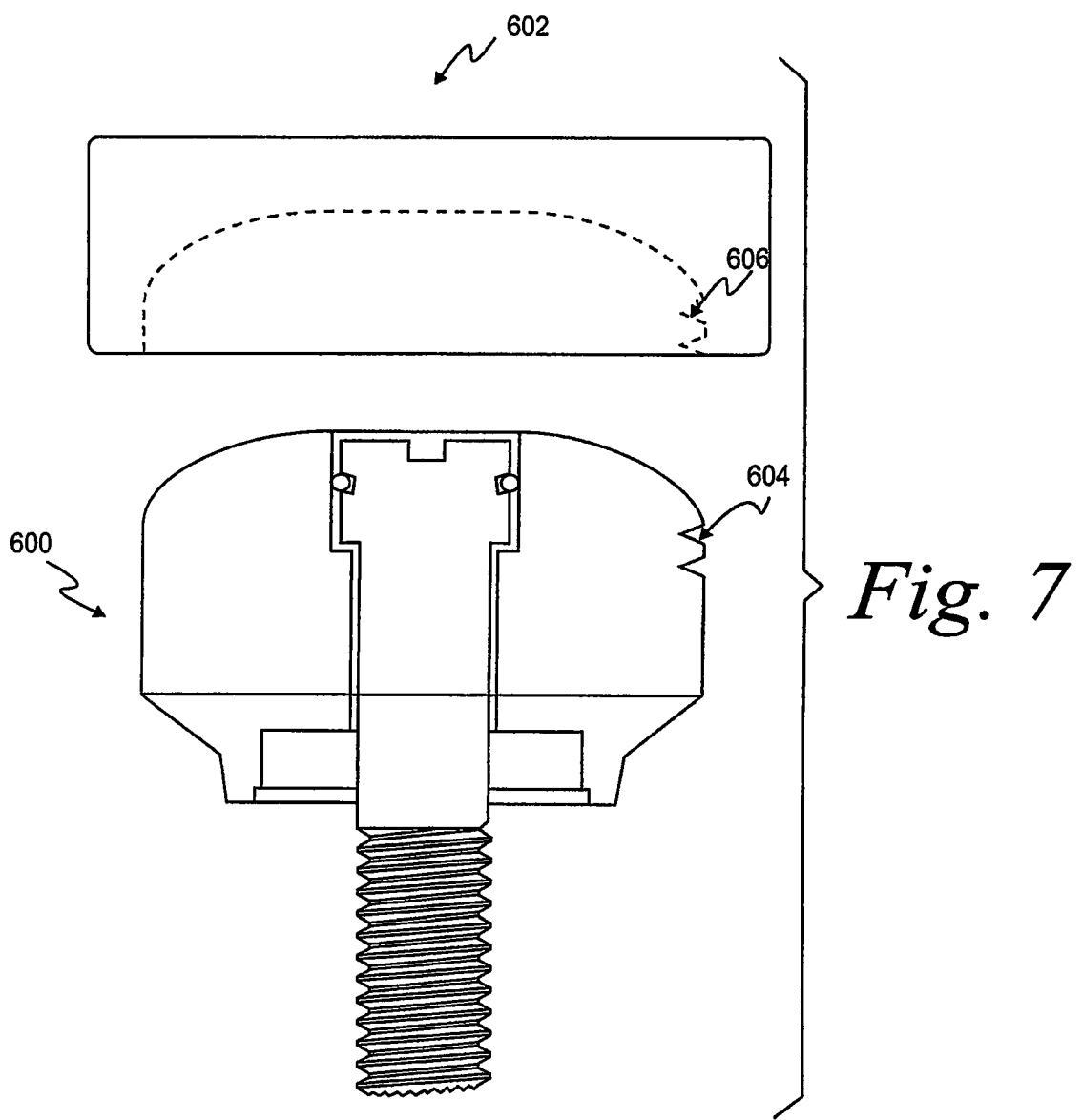
FIG. 7 is an exploded view of another embodiment of the present application.

FIG. 7 shows the exploded view of another embodiment of the present invention. A cap 602 is placed on a healing abutment 600 and later removed during the process of taking the impression of the healing implant and surrounding features of the patient's mouth. It is contemplated in accordance with the present invention that the cap 602 could be formed from plastic or metal or a composite material. As shown in FIG. 7, notches 604 are formed in the side(s) of the healing abutment 600. These notches correspond to notches 606 that have been preformed in the cap 602. When the cap 602 is placed onto the healing abutment 600, the cap only fits snugly and properly if the number of notches 606 in the cap 602 corresponds exactly to the number of notches 604 in the side wall(s) of the healing abutment. It is contemplated in accordance with the present invention that there could be many less or more notches than is depicted in FIG. 7. These notches correspond to information parameters such as healing abutment height, healing abutment and/or implant diameter and other parameters as listed above.

Specifically, after the healing abutment has been secured to the implant, the cap 602 is securely placed over the top of the healing abutment 600. The impression material is then placed over the top of the cap 602. The impression is then either scanned in the patient's mouth or the impression material (with the cap 602) is then scanned and the process continues as described above.

Figures 9A, 9B, 9C, 9D:
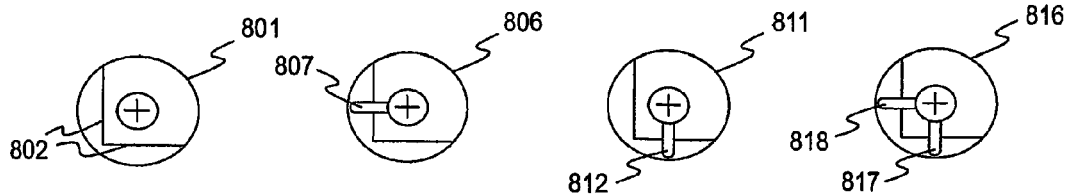
FIGS. 9a-9p are top views of a plurality of healing abutments having a binary-type system of information markers.
Figures 9E, 9F, 9G, 9H:
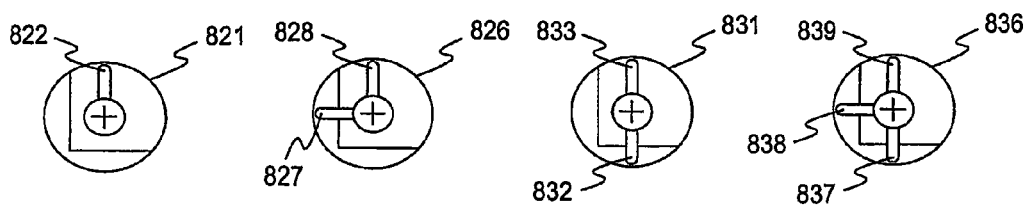
FIG. 9q is a top view of a healing abutment having a bar code information marker.
Figures 9I, 9J, 9K, 9L:
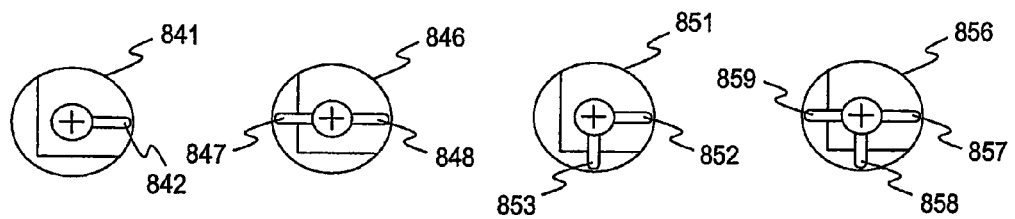
Figures 9M, 9N, 9O, 9P:
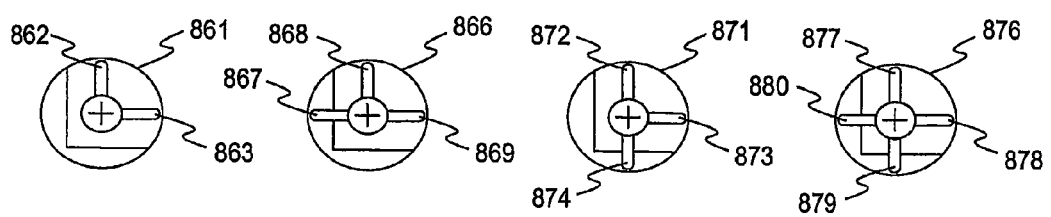

FIGS. 9a-9p depict yet another embodiment of the present invention. Specifically, FIGS. 9a-9p show the top view of a plurality of healing abutments, each of which has four marking locations on the top surface of the healing abutment. For each healing abutment, a marker is either present or absent in each of the four marking locations, and the presence or absence can be interpreted either visually or by a scanning device. As explained below in detail, the markers in the marking locations permit identification of healing abutment characteristics, such as dimensions of the healing abutment.

In FIGS. 9a-9p, the four rows correspond to four different healing abutment heights (e.g., 3 mm, 4 mm, 6 mm, and 8 mm). The four columns of the coding key correspond to four different diameters of the healing abutment seating surfaces (e.g., 3.4 mm, 4.1 mm, 5.0 mm, and 6.0 mm). Accordingly, sixteen unique healing abutments are present.

The top surface of each of the healing abutments has from zero to four information markers located in the four marking locations. As shown in FIGS. 9a-9p, the marking locations extend radially from a central region of the healing abutment to the outer region of the top surface of the healing abutments (i.e., at locations of 12 o'clock, 3 o'clock, 6 o'clock, and 9 o'clock).

As is well known, a binary-coded system exists as an array of digits, where the digits are either "1" or "0" that represent two states, respectively, ON and OFF. For each marking location, the presence of a marker ("ON") is a 1 and the absence of a marker ("OFF") is a 0. By grouping sets of 1's and 0's together, information about each healing abutment is known. In the illustrative embodiment, the determination of the sets of 1's and 0's derived from the information markers (e.g., via visual inspection, scanning in the mouth, scanning of the impression, or scanning of the model created by the impression) provide information on the height of the healing abutment and the diameter of the seating surface of the attached implant.

The information markers shown in FIGS. 9a-9p are in the form of grooves having rounded cross-sections. The present invention, however, provides that the cross-section of these grooves can be rectangular, triangular, or various other shapes. When an impression is created from the healing abutment, the grooved marking locations produce a protruding "mound"-like element in the impression. This impression is then scanned so that identifying features regarding the healing abutment can be obtained. Alternatively, a model of the patient's mouth is created from the impression such that the markings are again grooves in the model that substantially replicate the grooves in the healing abutments. Of course, the markers could also be protrusions instead of grooves. Further, if the unique characteristics of the healing abutment are to be identified through scanning in the mouth or simply visual scanning by the clinician, then markers not producing features in impression material, such as etched or laser marking, may also be used.

Turning now to the specifics of each healing abutment, FIG. 9a illustrates a top view of a healing abutment 801 that includes orientation pick-ups 802. These orientation pick-ups 802 are also present in each of the healing abutments shown in FIGS. 9b-9p. The most counterclockwise of the orientation pick-ups 802 (i.e., the horizontal pick-up at the lower region of FIGS. 9a-9p) is always parallel to one flat of the implant hex, as viewed from the top of the healing abutment. As shown, the orientation pick-ups 802 are a pair of bevels on the sides of the healing abutments in FIGS. 9a-9p. Alternatively, the orientation pick-ups 802 can be grooves or protruding ridges, as well.

The orientation pick-ups 802 serve a second function in that they dictate which of the four marking locations is the first marking location. The other three marking locations are then read in clockwise order, proceeding from the most counterclockwise pick-up 802 to the other three marking locations on the top surface of the healing abutment. In other words, as illustrated in FIGS. 9a-9p, the information marker at 6 o'clock is the first digit in the binary code, the information marker at 9 o'clock is the second digit in the binary code, the information marker at 12 o'clock is the third digit in the binary code, and the information marker at 3 o'clock is the fourth digit in the binary code. In summary, the position of the orientation pick-ups 802 allows for the determination of the position of one of the hex flats of the healing abutment (and, likewise, one of the hex flats on the implant), and also the starting point to check for the presence or absence of information markers.

The results of a scan (computer or visual) of the four information markers on the healing abutment 801 produce no information markers at the four marking locations on the healing abutment 801 of FIG. 9a. Thus, the binary code for the healing abutment 801 is 0000, indicating that no grooved marker is present in any of the four predetermined positions. Since the coding key is preset (on a chart or in computer software), the binary code 0000 indicates that the healing abutment 801 is a resident of first row and first column of the matrix depicted by FIG. 9, having a height of 3 mm and a seating surface diameter of 3.4 mm. Thus, the three distinct pieces of information obtained from the top of the healing abutment allow the clinician or laboratory to know (i) the orientation of the hex of the implant, (ii) the height of the healing abutment (i.e., the location of the implant's seating surface below the healing abutment), and (iii) the seating surface diameter of the healing abutment (or the size of the implant's seating surface).

The healing abutment 806 in FIG. 9b possesses a binary code of 0100 because only one information marker 807 is present in the second marking location. Thus, it is understood from the binary code that the healing abutment 806 is 3 mm in height and has a seating surface diameter of 4.1 mm. The two healing abutments 811, 816 in FIGS. 9c, 9d have binary codes of 1000 and 1100, respectively. Healing abutment 811 has an information marker 812 in the first marking location, while healing abutment 816 has information markers 817, 818 in the first two locations. Thus, the unique characteristics of these two healing abutments are known.

The healing abutments 821, 826, 831, 836 shown in FIGS. 9e-9h and having heights of 4 mm, but with varying seating surface diameters, would be interpreted as having binary codes 0010, 0110, 1010, and 1110, respectively. Healing abutment 821 has one information marker 822 present in the third marking location, thus resulting in a binary code of 0010, which is indicative of a healing abutment height of 4 mm and a seating surface diameter of 3.4 mm. Similar analyses on healing abutment 826 with information markers 827; 828, healing abutment 831 with information markers 832, 833, and healing abutment 836 with information markers 837, 838, 839 allow determinations of the unique characteristics of these healing abutments.

The healing abutments 841, 846, 851, 856 shown in FIGS. 9i-9l and having heights of 6 mm, but with varying seating surface diameters, would be interpreted as having binary codes 0001, 0101, 1001, and 1101, respectively. Healing abutment 841 has one information marker 842 present in the fourth marking location, thus resulting in a binary code of 0001, which is indicative of a healing abutment height of 6 mm and a seating surface diameter of 3.4 mm. Similar analyses on healing abutment 846 with information markers 847, 848, healing abutment 851 with information markers 852, 853, and healing abutment 856 with information markers 857, 858, 859 allow determinations of the unique characteristics of these healing abutments.

The healing abutments 861, 866, 871, 876 shown in FIGS. 9m-9p and having heights of 8 mm, but with varying seating surface diameters, would be interpreted as having binary codes 0011, 0111, 1011, and 1111, respectively. Healing abutment 861 has two information markers 862, 863, which is indicative of a healing abutment height of 8 mm and a seating surface diameter of 3.4 mm. Similar analyses on healing abutment 866 with information markers 867, 868, 869, healing abutment 871 with information markers 872, 873, 874, and healing abutment 876 with information markers 877, 878, 879, 880 allow determinations of the unique characteristics of these healing abutments.

While the matrix of the sixteen healing abutments in FIGS. 9a-9p show four implant seating surface diameters and four heights, the matrix could include other physical characteristics of the healing abutment. For example, the maximum diameter of the healing abutment could be information obtainable through the binary-coded system. The type of fitting on the healing abutment and, thus, the implant (i.e., internal hex or external hex) could be provided. Information unrelated to the healing abutment, but related to only the implant, could be used. For example, the manufacturer of the implant could be noted. Or, information regarding the type of screw that mates with the internally thread bore of the implant could be provided.

Further, while FIGS. 9a-9p demonstrate the ability of the four digit, binary-coded system to provide two physical characteristics of the healing abutment, it could provide three or more physical characteristics. For example, two seating surface sizes, four heights, and two maximum diameters would provide sixteen unique healing abutments. If more information were needed, a fifth marking location could be added to provide the opportunity for displaying thirty-two physical characteristics of the healing abutments and/or implant. And, while one marking location has been shown with marker, it is possible to have two or more markers in each marking location. For example, one circumferential groove and one radial groove within one location could represent two digits of a binary system. Alternatively, having two widths possible for each groove could provide additional indicia representative of certain information about the healing abutment.

While the invention has been described with round healing abutments, healing abutments anatomically shaped like teeth can take advantage of the information markers. Thus, the set of healing abutments could include components shaped like the various teeth, and the information markers could provide the information regarding which tooth shape is present on the healing abutment. For example, a set may include four types of molar-shaped healing abutments, four types of bicuspid-shaped healing abutments, four types of incisor-shaped healing abutments and four types of round abutments. The four information marker locations on each component in the set provide the information to determine which one of the sixteen healing abutments is being used.

It is contemplated that the present invention also covers a set of eight unique healing abutments (as opposed to the sixteen shown) requiring only three marking locations. The computer software and/or the visual chart in this situation would identify these eight unique healing abutments through binary codes possessing three digits. The potential binary codes corresponding to an ON or OFF determination at the three marking locations are 000, 100, 010, 001, 110, 101, 011, and 111. Similarly, if the set has only four unique healing abutments, only two marking locations would be required on the healing abutments to determine features regarding the healing abutment and the attached dental implant. The potential binary codes in a four healing abutment matrix are 00, 10, 01, and 11.

After the top surface of a healing abutment (or the impression of the top surface, or the model of the impression of the top surface) is analyzed, the orientation of the hex is known from the location of the orientation pick-ups 802 and, via the binary code, the abutment height and the seating surface of the healing abutment is known. Other information regarding the healing abutment and the attached implant can also be determined by adding other markers of the type previously shown.

Figure 9Q:
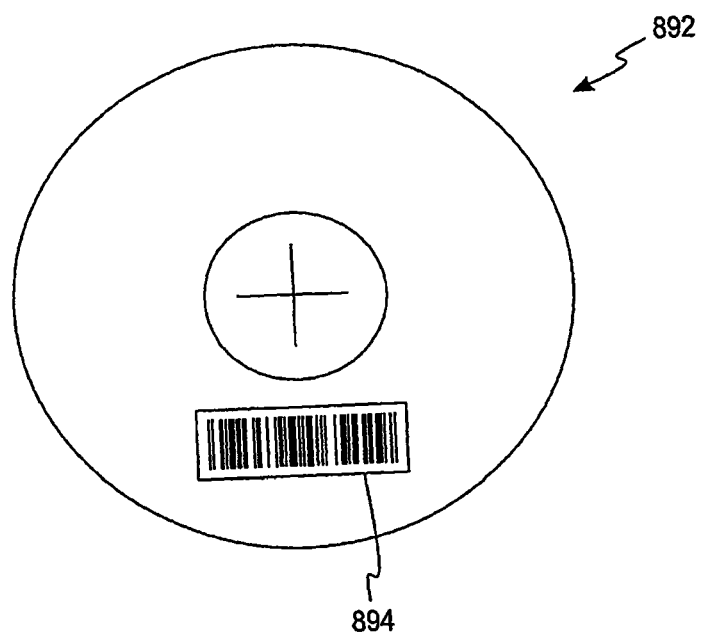

In addition to the markers described, it is further possible to provide a bar-coded system for providing information about the particular component, as shown in FIG. 9q. The bar code 894 can be located on the top surface on the healing abutment 892 such that it can be scanned or read easily. Thus, the bar code 894 would provide the same type of information described above with respect to the information markers.

Figure 10:
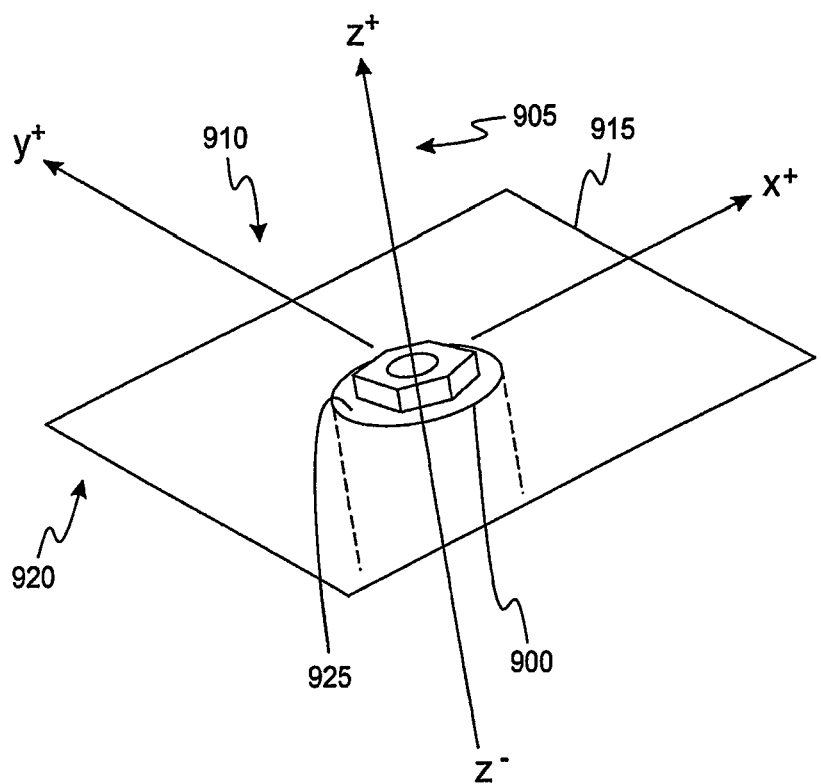
FIG. 10 is a perspective view of a coordinate system of one embodiment of the present invention.

Referring to FIG. 10, when scanning techniques are used to learn of the information on the top of the healing abutment, the computer software is able to determine the position and orientation of the implant 900 relative to the adjacent teeth. The position of the implant 900 is defined in a Cartesian coordinate system having "X," "Y," and "Z" axes. The common point is at the intersection of the centerline of the implant and a plane 920 representing the seating surface 925 of the implant 900.

As noted above, the information markers assist in determining the height of the healing abutment above the implant. This height can be used to identify the zero point on the "Z" axis, which is in the plane 920 containing the seating surface 925 of the implant 900. The "Y" axis 910 is within the plane 920 representing the seating surface 925 with the positive "Y" direction as close to the direction of facial to buccal as possible. The "X" axis 915 is in the plane 920 and is perpendicular to an implant hex face. Thus, the width of the seating surface 925 in the plane 920 is known, as is the width of the healing abutment emerging through the gingiva. Thus, the emergence profile of the artificial tooth is known, as well.

Figure 11:
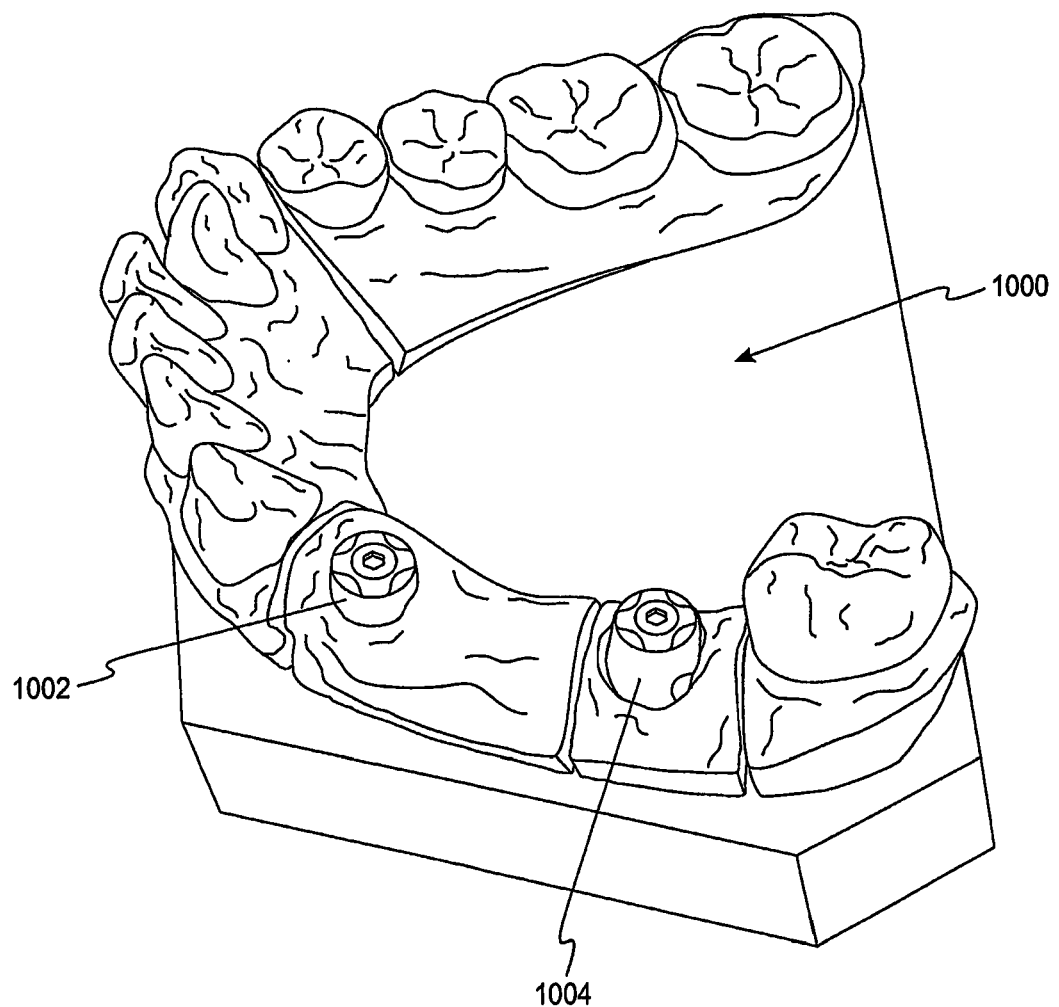
FIG. 11 is a perspective view of a stone model of an impression of a mouth according to one embodiment of the present invention.

Turning now to FIG. 11, a perspective view of a stone cast 1000 of a mouth of a patient is shown with two stone-cast models of healing abutments 1002, 1004, which have configurations on their upper surface that correspond to the healing abutments previously described. The stone cast 1000 is made from an impression of the mouth as previously described.

Figure 12:
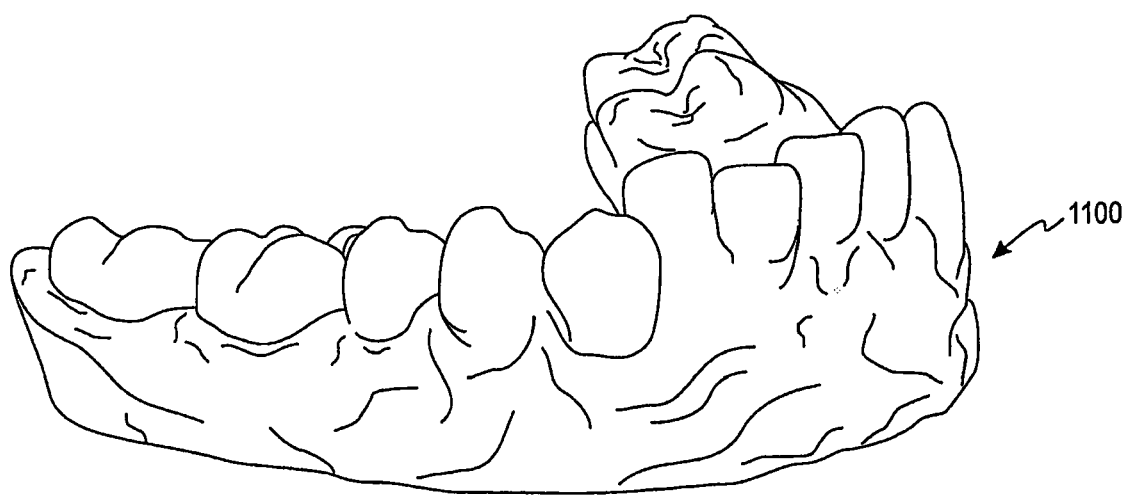
FIG. 12 is a perspective view of a 3-D CAD model of the stone model of FIG. 11.

Once the stone cast 1000 is prepared it is scanned using a scanning technique previously described, the scanned data is transferred into a graphical imaging program, such as a Computer Aided Design ("CAD") program so that a three-dimensional ("3-D") CAD model 1100 of the stone cast 1000 is created, as shown in FIG. 12.

Figure 13:
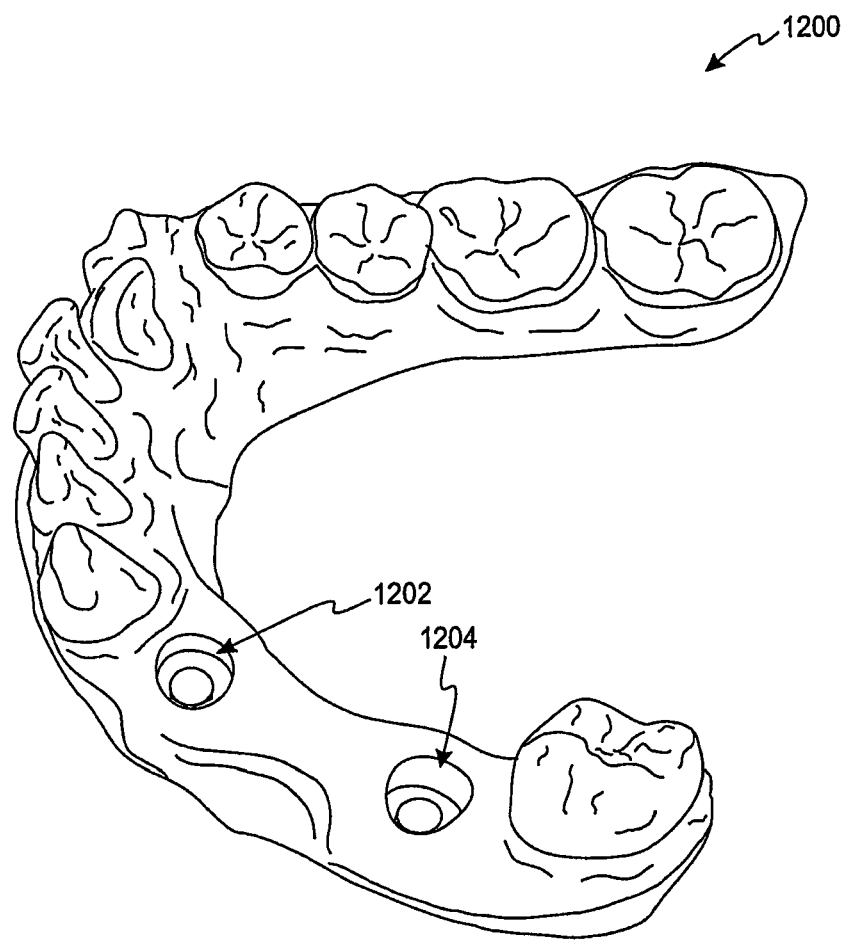
FIG. 13 is a perspective view of an altered 3-D CAD model of FIG. 12 with the healing abutments removed from the CAD model.

Using the CAD program, the 3-D CAD model 1100 is processed such that a first altered 3-D CAD model 1200 is created, as depicted in FIG. 13. The CAD program (or the operator of the CAD program) identifies the healing abutments (1002, 1004 from the stone cast 1000 of FIG. 11) from the cast 1000 so that the physical structure of the healing abutments may be removed from the first altered 3-D CAD model 1200. The first altered 3-D CAD model 1200 contains the implant seating surfaces 1202, 1204 corresponding to the dental implants to which the healing abutments (1002, 1004 from the stone cast 1000 of FIG. 11) are attached. The CAD program preferably contains the geometry of a plurality of possible implants, and models the upper surface of the implant underlying the healing abutments based on the markings contained on the healing abutments and/or information provided by the clinician.

Figure 14:
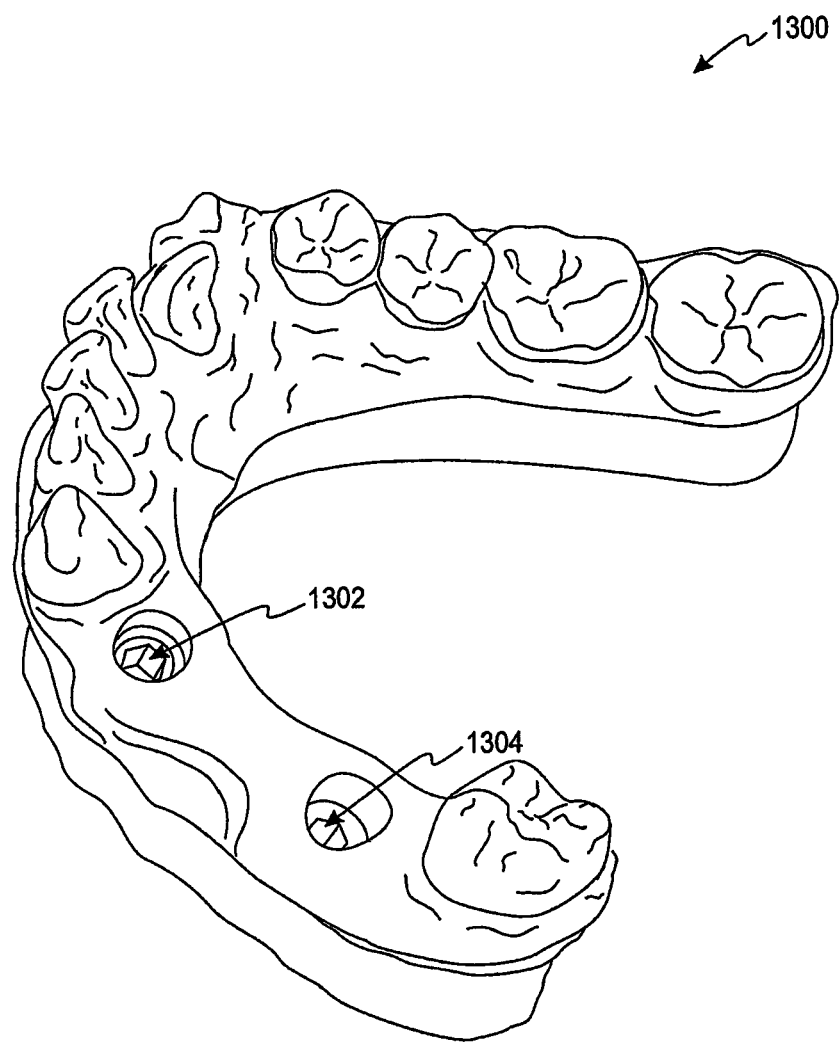
FIG. 14 is a perspective view of an altered 3-D CAD model of FIG. 13 with implant analog receptacles added in the CAD model.

The CAD program further modifies the first altered 3-D CAD model 1200 by removing the implant seating surfaces 1202, 1204 and replacing them in a second altered 3-D CAD model 1300 with implant analog receptacles 1302, 1304 as shown in FIG. 14. The CAD program contains the geometry of a plurality of possible implant analog receptacles corresponding to the plurality of implant analogs that may be used with the system. Each of the implant analog receptacles 1302, 1304 is adapted to receive an implant analog that is used in later steps to develop the tooth-like ceramic restoration on the custom abutment.

Once the second altered 3-D CAD model 1300 is created, the CAD program allows a rapid prototype 1400 (FIG. 15) corresponding to the second altered 3-D CAD model 1300 to be created using rapid prototype equipment. It is contemplated that many rapid prototyping techniques may be utilized with the present invention such as: stereolithography, laminated-object manufacturing, selective laser sintering, solid ground curing, or other known rapid prototyping processes. The second altered 3-D CAD model 1300 is used by the equipment controlling the rapid prototype equipment to create the rapid prototype 1400.

Figure 15:
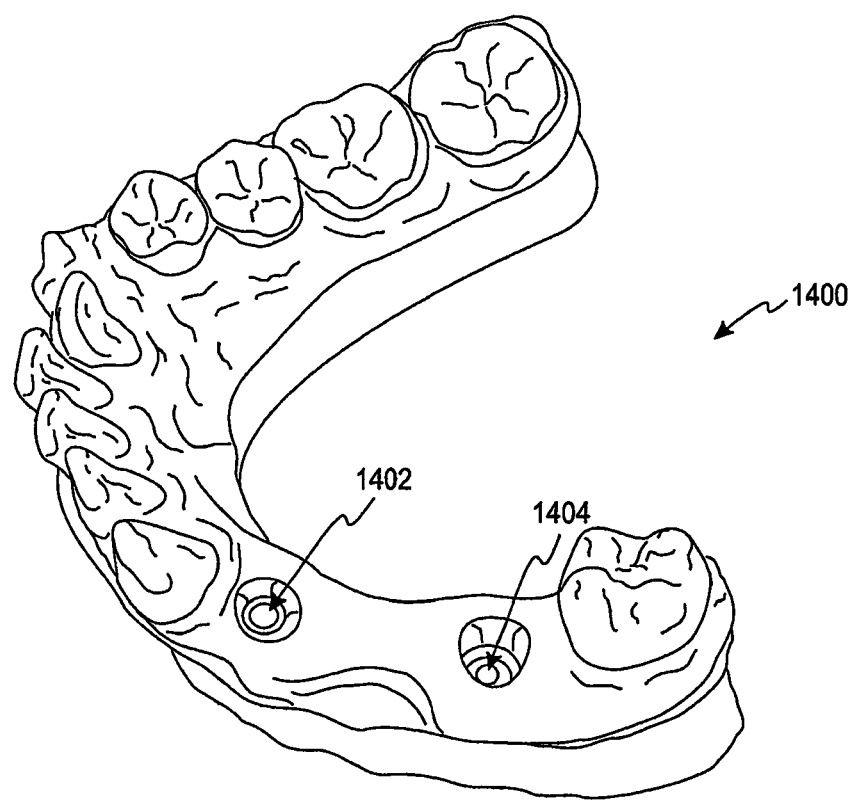
FIG. 15 is a perspective view of a rapid prototype model of the 3-D CAD model of FIG. 14 with implant analog receptacles.
Figure 24:
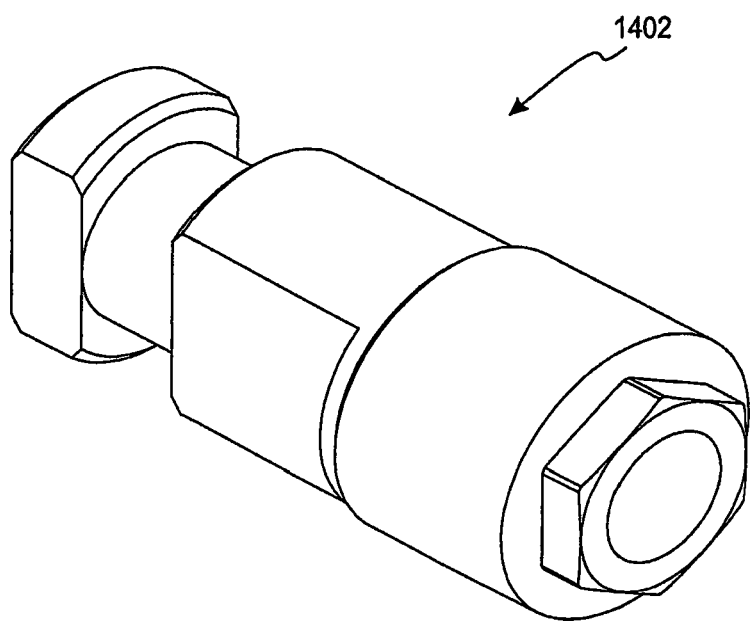
FIG. 24 is a perspective view of an implant analog used in conjunction with the present invention.

The rapid prototype 1400 is depicted in FIG. 15 and contains implant analogs 1402 (See FIG. 24), 1404 in respective implant analog receptacles 1302, 1304 of the second altered 3-D CAD model 1300. The implant analogs 1402, 1404 may be identical, or may vary depending on the implants placed in the patient. The implant analogs 1402, 1404 mimics the external geometry of at least a portion of an implant placed in a patient. The rapid prototype 1400 may then be sent to a dental lab to be utilized by the dental lab, along with the custom abutment as previously described, so that a permanent, or temporary, prosthesis to fit over the custom abutment may be produced. Utilizing the rapid prototype 1400 increases the accuracy of the prosthesis compared to using a duplicate stone cast to create the prosthesis. The rapid prototype 1400 contains implant analogs with highly accurate placement and orientation, as human error is removed from the placement of the implant analogs in a duplicate cast stone model. Additionally, the use of the rapid prototype 1400 does not require the creation of an implant-level impression, also referred to as a surgical index. Therefore, the healing abutments in the patient's mouth do not need to be removed to create such an impression and the healing process is enhanced.

It is further contemplated that the rapid prototype created from the second altered 3-D CAD model would additionally contain a rapid prototype of a custom patient-specific abutment. Such a rapid prototype would not contain an implant analog, but instead the dental lab could simply create a permanent, or temporary, prosthesis directly from the rapid prototype without having to assemble any components to the rapid prototype. This removes yet another step where human error may occur that could adversely affect the accuracy of the prosthesis.

Additionally, it is contemplated that a rapid prototype created from the second altered 3-D CAD model would contain a rapid prototype of a modified implant analog rather than an implant analog receptacle. The modified implant analog placed into the rapid prototype would have a blind hole to allow a self-tapping screw to be used to secure an abutment to the rapid prototype. The dental lab would then be able to a permanent, or temporary, prosthesis. The use of the self-tapping screw and the blind hole allow eliminates the need to create threads in the rapid prototype of the implant analog, thus simplifying the rapid prototype.

Figure 16:
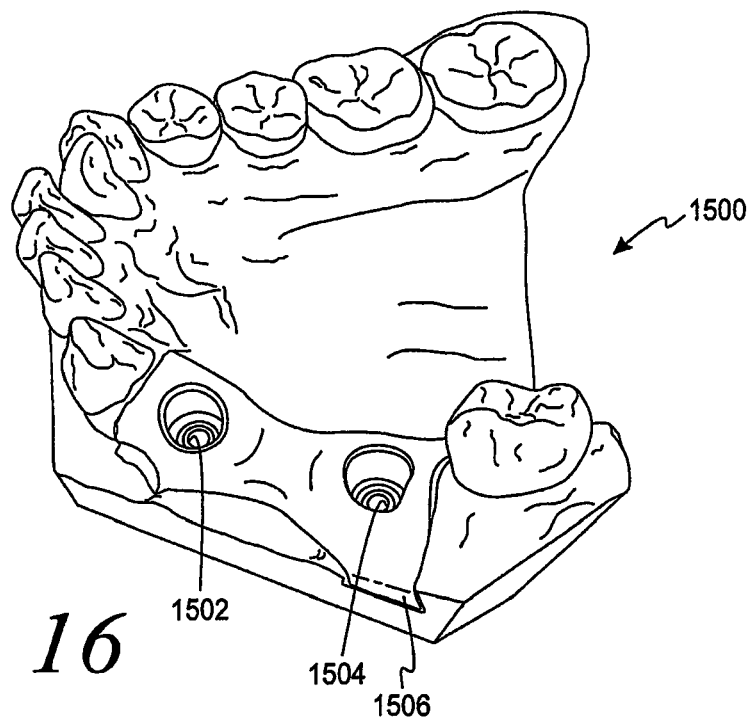
FIG. 16 is a perspective view of a stone model of an impression of a mouth with a soft tissue insert according to a further embodiment of the present invention.
Figure 17:
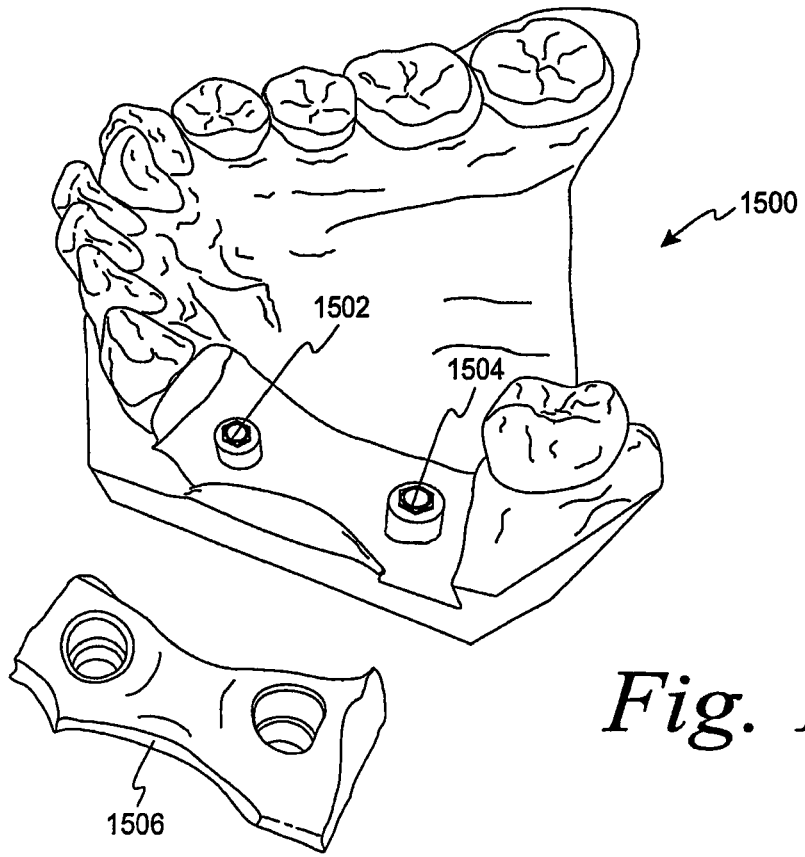
FIG. 17 is an exploded view of the stone model of FIG. 16.

Turning now to FIG. 16, a stone cast 1500 is shown having implant analogs 1502, 1504 inserted into the stone cast 1500 having a soft tissue element 1506. The soft tissue element 1506 simulates tissue in a patient's mouth. Soft tissue elements are explained in greater detail in U.S. Pat. Nos. RE 36,126 and RE 36,689, both of which are herein incorporated by reference in their entirety. FIG. 17 shows an exploded view of the stone cast 1500 with the soft tissue element 1506 removed.

Figure 18:
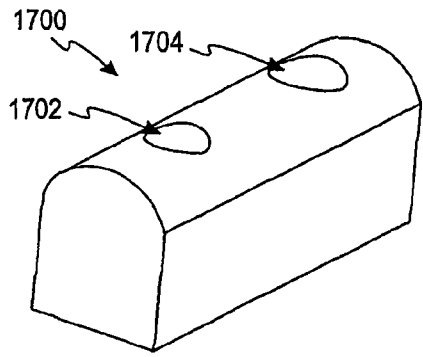
FIG. 18 is a partial perspective view of a 3-D CAD model of a stone model of a mouth.
Figure 19:
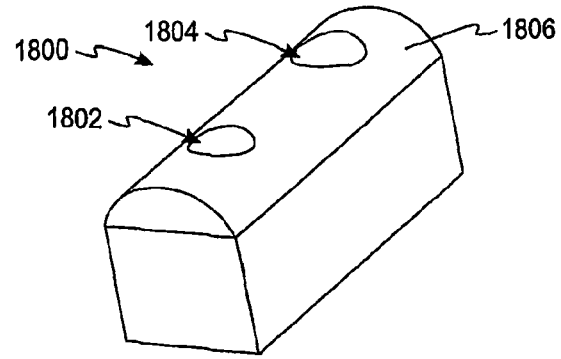
FIG. 19 is a partial perspective view of an altered 3-D CAD model of FIG. 18 with a soft tissue insert.

In order to create a stone model of a patient's mouth having both a soft tissue element and a more traditional dental stone material section, more than one material must be used when forming the model of the patient's mouth. Thus, the portion of the stone model around the dental implant will contain soft tissue model material, such as silicone, and the rest of the stone model contains traditional stone die material. The soft tissue model is typically removable from the rest of the stone model. FIG. 18 depicts a 3-D CAD model 1700 of a part of the region of a stone model containing implant analog receptacles 1702, 1704 that does not contain a soft tissue element. The CAD program is used to modify the 3-D CAD model 1700 to create a modified 3-D CAD model with a soft tissue element 1800 containing implant analog receptacles 1802, 1804 as well as a soft tissue element 1806, as depicted in FIG. 19. The modified 3-D CAD model with a soft tissue element 1800 may be utilized to create a cast 1816 (FIG. 22) of the soft tissue element 1806 as well as the underling stone material 1822.

Figure 20:
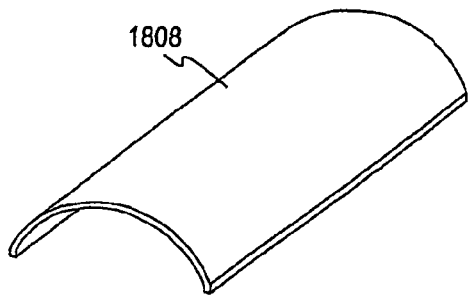
FIG. 20 is a perspective view of a first piece of a mold of the 3-D CAD soft tissue insert of FIG. 18.
Figure 21:
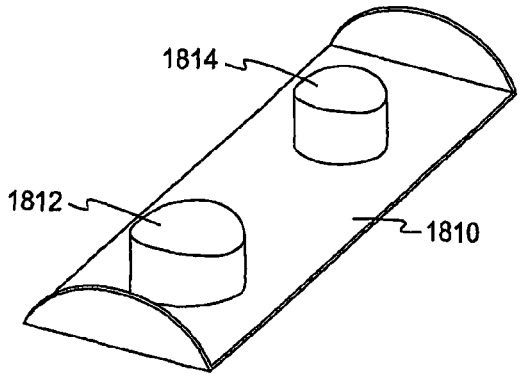
FIG. 21 is a perspective view of a second piece of a mold of the 3-D CAD the soft tissue insert of FIG. 18.
Figure 22:
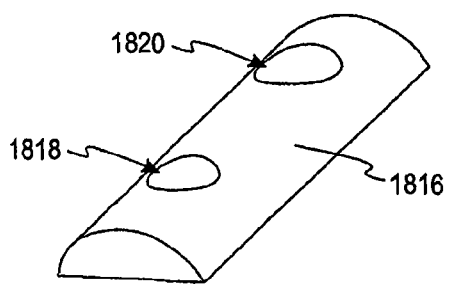
FIG. 22 is a perspective view of a soft tissue insert produce from the molds of FIGS. 20 and 21.
Figure 23:
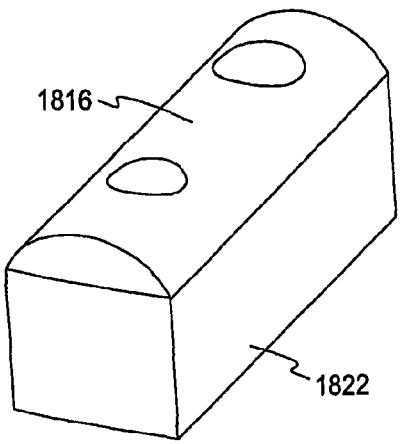
FIG. 23 is a partial perspective view of a rapid prototype model of the 3-D CAD model of FIG. 19.

The first step in creating the cast 1816 of the soft tissue element 1806 is to utilize the CAD program to generate a 3-D CAD model of a mold of the soft tissue element. As previously described, the CAD program obtains the location of the seating surfaces of the implants, and further modifies the CAD model to locate implant analog receptacles on the CAD model. Having the proper position of the implant analogs allows the CAD program to determine the position of the soft tissue element to be used with the particular 3-D CAD model. This allows the CAD program to calculate the locations, dimensions, and volume of the soft tissue element 1806. It is contemplated that the mold used to create the cast 1816 of the soft tissue element would be a two-piece mold. The first mold piece 1808, depicted in FIG. 20, controls the shape of the top outer surface of the cast of the soft tissue element 1816. The second mold piece 1810, shown in FIG. 21 controls the shape of the bottom outer surface of the cast of the soft tissue element 1816. The second mold piece 1810 contains through-hole elements 1812, 1814 to allow the cast of the soft tissue element 1816 to allow access to the implant analogs. The first mold piece 1808 and the second mold piece 1810 may be produced using rapid prototype equipment previously described. The completed first mold piece 1808 and second mold piece 1810 are assembled and the soft tissue material is poured into the assembled mold and the cast of the soft tissue element 1816 is created. FIG. 22 depicts the cast of the soft tissue element 1816. The soft tissue element 1816 has through-hole elements 1818 and 1820 so that the implant analogs in an underlying rapid prototype 1818 of a patient's mouth may be accessed. The soft tissue element 1816 is attached to the modified rapid prototype 1822 of the patient's mouth. The rapid prototype 1822 is created by a similar method to that previously described in relation to FIGS. 11-15, except an area to attach the soft tissue element 1816 is created by removing a portion of the stone material from the 3-D CAD model 1700 to accommodate the soft tissue element 1816.

According to an alternate embodiment of the present invention, a soft tissue element may be made directly on a rapid prototype machine. In such an embodiment the previously described molds would not be used, rather a compliant rapid prototype material would be used to form the soft tissue element directly on the rapid prototype machine.

According to an alternate embodiment of the present invention, Computed Tomography ("CT") technology is used in place of the previously described scanning to generate a 3-D model of a patient's mouth. Using the CT technology allows the use of any abutment, removing the requirement that the abutment contain markings like those found in FIGS. 1-6, and 9. To use the CT method, an implant is first placed within bone and allowed to osseointegrate. A healing abutment is then placed on the implant. A CT scan of the patient's mouth is then performed, generating CT scan data. The CT scan data is next used in combination with medical imaging and CAD programs to generate a 3-D CAD model of a patient's mouth. Once the 3-D CAD model of the patient's mouth is created, a rapid prototype of the patient's mouth may be generated in one of the methods previously described. Additionally, the custom abutment may be manufactured using the data obtained from the CT scan. The CT method eliminates the need to take an impression of the patient's mouth and to make a stone model of the patient's mouth for creating the final, or temporary, prosthesis. The elimination of the taking the impression and making the stone model improves the accuracy of the rapid prototype of the patient's mouth by eliminating the chance to introduce error into the rapid prototype when the impression is taken or when the stone model is created.

According to another alternate embodiment of the present invention, an intra-oral scanning technique is used. Instead of taking a scan of a stone model of the patient's mouth, a scan is taken within a patient's mouth that shows the patient's teeth and the healing abutment with a marking, such as those described in connection with FIGS. 1-6, and 9. Once the intra-oral scan is complete, the data generated is fed into the CAD program to create a 3-D CAD model of the patient's mouth. The rapid prototype methods described in connection with FIGS. 11-23 may then be performed to create a rapid prototype model of the patient's mouth so that a permanent, or temporary, prosthesis may be formed. The use of intra-oral scanning eliminates the need to take an impression of the patient's mouth and make a stone model of the patient's mouth. Eliminating these steps reduces the chance to introduce error into the rapid prototype when the impression is taken or when the stone model is created.

In addition to CT scanning, it is possible that an ultrasonic scan may be used to obtain ultrasonic scan data to be used to generate a 3-D CAD model of a patient's mouth. Using an ultrasonic technique to generate a model of a patient's mouth is disclosed in U.S. Pat. Nos. 6,050,821 and 6,638,219, each of which is incorporated by reference herein in its entirety.

In addition to milling a custom abutment from a metallic material, utilizing a process of the present invention, it is further contemplated that a polymeric custom abutment, such as an acrylic custom abutment, may be made from a 3-D CAD model. The acrylic custom abutment may be used as a temporary prosthetic abutment. It is additionally contemplated that additional components, such as a custom healing abutment may be manufactured utilizing a method of the present invention. A temporary polymeric custom abutment may be useful in allowing the temporary polymeric abutment to be used in a patient while a metallic custom abutment is manufactured, or to allow gingival healing or gingival sculpting.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of creating a prosthetic tooth to be placed on a dental implant, comprising:
   receiving scan data from a patient's mouth, the scan data including information about the location of the dental implant installed in the patient's mouth;
   using a computer, developing a computer model of the patient's mouth from the scan data;
   by use of the computer model, developing a first data set to be used in developing a rapid-prototype physical model, the rapid-prototype physical model having a receptacle for receiving an implant analog at a location corresponding to the implant installed in the patient's mouth;
   providing the implant analog to be placed in the receptacle of the rapid-prototype physical model, the implant analog having features corresponding to the installed dental implant;
   by use of the computer model, developing a second data set to be used in developing a custom dental abutment to be placed on the dental implant in the patient's mouth; and
   manufacturing the custom dental abutment by use of the second data set, the custom dental abutment to be attached to the implant analog after the implant analog has been installed in the receptacle in the rapid-prototype physical model so as to allow for the fabrication of a tooth-like restoration on the custom dental abutment, the prosthetic tooth comprising the tooth-like restoration and the custom dental abutment.

2. The method of claim 1, further including selecting the implant analog from a plurality of implant analogs.

3. The method of claim 2, wherein the receptacle is made to correspond to the selected implant analog.

4. The method of claim 1, wherein the implant analog includes an exposed external geometry that mimics the external geometry of the dental implant.

5. The method of claim 4, wherein the exposed external geometry of the dental implant analog is located within the receptacle extending into the rapid prototype model.

6. The method of claim 1, wherein the fabrication of the tooth-like restoration includes attaching the custom dental abutment on the implant analog and fitting the tooth-like restoration on the custom dental abutment.

7. The method of claim 1, further including fabricating, by use of the first data set, the rapid-prototype physical model and placing the implant analog in the receptacle.

8. The method of claim 1, wherein the information about the location of the dental implant is derived from a scannable member attached to the dental implant.

9. The method of claim 8, wherein the scannable member includes at least one information marker for providing the information about the dental implant.

10. The method of claim 9, wherein the at least one information marker includes a geometrically shaped surface on the scannable member.

11. The method of claim 10, wherein the geometrically shaped surface on the scannable member indicates a position of an anti-rotational feature of the implant.

12. The method of claim 11, wherein the custom dental abutment has a feature for mating with the anti-rotational feature of the implant.

13. The method of claim 8, wherein the scannable member is a healing abutment.

14. A method of creating a prosthetic tooth to be placed on a dental implant, comprising:
   receiving, at a computer, scan data from a patient's mouth, the scan data including information about the location of the dental implant installed in the patient's mouth;
   by use of graphical design software associated with the computer, developing a virtual model of the patient's mouth from the scan data, the virtual model being displayed on a display associated with the computer;
   by use of the graphical design software, developing a first data set to be used in developing a rapid-prototype physical model, the rapid-prototype physical model having a receptacle for receiving an implant analog at a location corresponding to the dental implant installed in the patient's mouth, the implant analog having features corresponding to the installed dental implant;
   by use of the graphical design software, developing a second data set to be used in developing a custom dental abutment that is for placement on the dental implant in the patient's mouth; and
   by use of the second data set, manufacturing the custom dental abutment, the custom dental abutment to be attached to the implant analog that has been installed in the receptacle in the rapid-prototype physical model so as to allow the fabrication of a tooth-like restoration on the custom dental abutment, the prosthetic tooth comprising the tooth-like restoration and the custom dental abutment.

15. The method of claim 14, wherein the information about the location of the implant is derived from a scannable member attached to the dental implant.

16. The method of claim 15, wherein the scannable member includes at least one information marker for providing information about the dental implant.

17. The method of claim 16, wherein the at least one information marker includes a geometrically shaped surface on the scannable member.

18. The method of claim 17, wherein the geometrically shaped surface on the scannable member indicates a position of an anti-rotational feature of the implant.

19. The method of claim 18, wherein the custom dental abutment has a feature for mating with the anti-rotational feature of the implant.

20. The method of claim 15, wherein the scannable member is a healing abutment.

21. The method of claim 14, further including fabricating, by use of the first data set, the rapid-prototype physical model and placing the implant analog in the receptacle.

22. The method of claim 21, further including adding a compliant soft tissue element to a region of the rapid-prototype physical model adjacent to the implant analog.

23. The method of claim 22, wherein the material comprising the compliant soft tissue element is different from a base material of the rapid prototype model and is made by a rapid prototype technique.

24. The method of claim 22, wherein the compliant soft tissue element surrounds the implant analog and includes a through-hole leading to the implant analog, the through-hole being at least a portion of the receptacle.

25. The method of claim 7, further including adding a compliant soft tissue element to a region of the rapid-prototype physical model adjacent to the implant analog.

26. The method of claim 25, wherein the material comprising the compliant soft tissue element is different from a base material of the rapid prototype model and is made by a rapid prototype technique.

27. The method of claim 25, wherein the compliant soft tissue element surrounds the implant analog and includes a through-hole leading to the implant analog, the through-hole being at least a portion of the receptacle.

28. A method of creating a prosthetic tooth to be placed on a dental implant, comprising:

receiving, at a computer, scan data from a patient's mouth, the scan data including data corresponding to scannable member coupled to the dental implant, the data from the scannable member providing information about the location of the dental implant installed in the patient's mouth;

by use of graphical design software associated with the computer, developing a virtual model of the patient's mouth from the scan data, the virtual model being displayed on a display associated with the computer;

by use of the graphical design software, developing a first data set to be used in developing a rapid-prototype physical model, the rapid-prototype physical model having a receptacle in which an implant analog structure is to be positioned at a location corresponding to the dental implant installed in the patient's mouth, the implant analog structure having features corresponding to the installed dental implant;

by use of the graphical design software, developing a second data set to be used in developing a custom dental abutment that is for placement on the dental implant in the patient's mouth, the custom dental abutment being a part of the prosthetic tooth; and fabricating, by use of the first data set, the rapid-prototype physical model having the implant analog structure in the receptacle to be mated with the custom dental abutment in creating the prosthetic tooth.

29. The method of claim 28, further including, by use of the second data set, manufacturing the custom dental abutment, the custom dental abutment to be attached to the implant analog structure in the receptacle in the rapid-prototype physical model so as to allow the fabrication of a tooth-like restoration on the custom dental abutment, the prosthetic tooth comprising the tooth-like restoration and the custom dental abutment.

30. The method of claim 28, furthering including providing an implant analog and fitting the implant analog into the receptacle in the rapid-prototype physical model, the implant analog providing the implant analog structure.

31. The method of claim 28, wherein the fabricating the rapid-prototype physical model includes adding a soft tissue element surrounding the implant analog structure.

32. The method of claim 31, wherein the soft tissue element is made by a rapid prototype technique.

* * * * *